US006720152B1

(12) United States Patent
Weil et al.

(10) Patent No.: US 6,720,152 B1
(45) Date of Patent: Apr. 13, 2004

(54) DIAGNOSIS OF HISTOPLASMOSIS USING ANTIGENS SPECIFIC FOR H. CAPSULATUM

(75) Inventors: Gary J. Weil, Creve Couer, MO (US); Ramaswamy Chandrashekar, Fort Collins, CO (US)

(73) Assignee: Barnes-Jewish Hospital, St. Louis, MO (US)

( * ) Notice: Subject to any disclaimer, the term of this patent is extended or adjusted under 35 U.S.C. 154(b) by 0 days.

(21) Appl. No.: 09/060,767

(22) Filed: Apr. 15, 1998

Related U.S. Application Data

(60) Provisional application No. 60/043,332, filed on Apr. 15, 1997.

(51) Int. Cl.[7] ...................... G01N 33/53; G01N 33/558

(52) U.S. Cl. ....................... 435/7.1; 435/7.2; 435/7.31; 435/7.92; 435/7.93; 436/514; 436/536

(58) Field of Search .......................... 424/130.1, 139.1, 424/141.1, 184.1, 191.1, 274.1, 93.5; 435/4, 6, 7.1, 7.2, 7.31, 7.92, 243, 254.1, 255.1, 255.4; 536/23.1, 23.7, 23.74; 935/1, 6, 18, 19, 76, 77; 436/514, 536

(56) References Cited

U.S. PATENT DOCUMENTS 5,279,960 A 1/1994 Anderson et al. ........... 435/243

OTHER PUBLICATIONS

Zancope—Oliveira et al. Clinical and Diagnostic Laboratory Immunolog–1, 1(4):390–393, 1994.*

Hamilton et al. Joiurnal of General Microbiology 136:331–335, 1990.*

Peterson et al., "Detection of Candidal Antigens in Auto–immune Polyglandular Syndrome Type I"; Clin. Diag. Lab. Immunol. 3:290–294 (1996).

Clark et al., "Enzyme–Linked Immunosorbent Assay (ELISA): Theoretical and Practical Aspects", pp. 167–178 in Enzyme–Immunoassay, Edward T. Maggio, ed. CRC Press, Inc. (1987).

Galfre, et al.; Antibodies to Major Histocompatibility Antigens Produced by Hybrid Cell Lines; Nature vol. 266:550–552 (1977).

Lowman, et al.; Selecting High–Affinity Binding Proteins by Monovolant Phage Display; Biochemistry (1991):10832–10838.

Zimmerman, et al.; Cloning and Expression of the Complement Fixation Antigen–Chitinase of *Coccidioides immitis;* Infection and Immunity, Dec. 1996, p. 4967–4975.

Wheat, J.; "Histoplasmosis: Experience During Outbreaks in Indianapolis and Review of the Literature"; Medicine 76:339–354 (1997).

Chandrashekar et al.; "Molecular Cloning and Characterization of a Recombinant *Histoplasma capsulatum* Antigen for Antibody–Based Diagnosis of Human Histoplasmosis"; J. Clin. Microbiol. 35:1071–1076 (1997).

Yang et al.; "Mapping of a *Coccidioides immitis*–Specific Epitope that Reacts with Complement–Fixing Antibody"; Infection and Immunity 65:4068–4074 (1997).

Gomez et al.; "Development of a Novel Antigen Detection Test for Histoplasmosis"; J. Clin. Microbiol. 35:2618–2622 (1997).

Durkin et al.; "Comparison of Radioimmunoassay and Enzyme–Linked Immunoassay methods for Detection of *Histoplasma capsulatum* var. *capsulatum* Antigen"; J. Clin. Microbiol. 35:2252–2255 (1997).

Yang et al.; "Recombinant *Coccidioides immitis* Complement–Fixing Antigen: Detection of an Epitope Shared by *C. immitis, Histoplasma capsulatum,* and *Blastomyces dermatitidis";* Clin. Diag. Lab. Immunol. 4:19–22 (1997).

Wheat et al.; "Cross–reactivity in *Histoplasma capsulatum* variety *capsulatum* Antigen Assays of Urine Samples from Patients with Endemic Mycoses"; Clinical Infectious Diseases 24:1169–1171 (1997).

Johnson et al.; "Use of a Recombinant *Coccidioides immitis* Complement Fixation Antigen–Chitinase in Conventional Serological Assays"; J. Clin. Microbiol. 34:3160–3164 (1996).

"*Ajellomyces Capsulatum* Immunoreactive Clone GH17 mRNA, Complete cds"; GenBank Accession No. U27588; Jun. 28, 1995.

Chandrashekar et al.; "Molecular Cloning of *Brugia malayi* antigens for Diagnosis of Lymphatic Filariasis"; Mol. Biochem. Parasitol. 64:261–271 (1994).

de Repentigny, L.: "Serodiagnosis of Candidiasis, Aspergillosis, and Cryptococcosis"; Clinical Infectious Diseases 14(Suppl 1): S11–S22 (1992).

Hauser et al.; "P–domains as Shuffled Cysteine–rich Modules in Integumentary Mucin C.1 (FIM–C.1) from *Xenopus laevis.* Polydispersity and Genetic Polymorphism"; J. Biol. Chem. 267:24620–24624 (1992).

Kaufman, L.; "Laboratory Methods for the Diagnosis and Confirmation of Systemic Mycoses"; Clin. Infect. Dis. 14:S23–S29 (1992).

(List continued on next page.)

*Primary Examiner*—Patricia A. Duffy
(74) *Attorney, Agent, or Firm*—Sonnenschein Nath & Rosenthal

(57) ABSTRACT

A method for identifying a protein antigen to a target fungus is disclosed. The method comprises screening expressed proteins from a cDNA gene expression library with antisera to the target fungus and cross-screening with antisera to a nontarget fungus. Antibodies to the protein antigen are also disclosed. Methods for detecting the presence or absence of the antibodies or of the protein antigen are also disclosed, as well as kits for performing such assays. In preferred embodiments, the target fungus is *H. capsulatum.*

9 Claims, 6 Drawing Sheets

OTHER PUBLICATIONS

Lustigman et al.; "Characterization of an *Onchocerca volvulus* cDNA Clone Encoding a Genus–specific Antigen Present in Infective Larvae and Adult Worms"; Mol. Biochem. Parasitol. 45:65–76 (1991).

Luthi et al.; "Cloning, Sequence Analysis, and Expression in *Escherichia coli* of a Gene Coding for a β–Mannanase from the Extremely Thermophilic Bacterium *Caldocellum saccharolyticum*"; Appl. Environ. Microbiol. 57:694–700 (1991).

Murray et al.; "Variants of a Leishmania Surface Antigen Derived from a Multigenic Family"; J. Biol. Chem. 266:24477–24484 (1991).

Lobos et al.; "An Immunogenic *Onchocerca volvulus* Antigen: A Specific and Early Marker of Infection"; Science 251:1603–1605 (1991).

Chandrashekar et al.; "Molecular Cloning and Characterization of Recombinant Parasite Antigens for Immunodiagnosis of Onchocerciasis"; J. Clin. Invest. 88:1460–1466 (1991).

Spitzer et al.; "Temperature–sensitive Variants of *Histoplasma capsulatum* Isolated from Patients with Acquired Immunodeficiency Syndrome"; J. Infect. Dis. 162:258–161 (1990).

Keath et al.; "Variable Expression of a Yeast–phase–specific Gene in *Histoplasma capsulatum* Strains Differing in Thermotolerance and Virulence"; Infect. Immun. 57:1384–1390 (1989).

Wheat et al.; "*Histoplasma capsulatum* Polysaccharide Antigen Detection in Diagnosis and Management of Disseminated Histoplasmosis in Patients with Acquired Immunodeficiency Syndrome"; Am. J. Med. 87:396–400 (1989).

Wheat et al.; "Significance of Histoplasma Antigen in the Cerebrospinal Fluid of Patients with Meningitis"; Arch. Intern. Med. 149:302–304 (1989).

Rao et al.; "A Serendipitous Isolate of *Histoplasma capsulatum*"; Pathology 20:191–193 (1988).

Lambert et al.; "Evaluation of Enzyme Immunoassay as a Rapid Screening Test for Histoplasmosis and Blastomycosis"; Am. Rev. Resp. Dis. 136:316–319 (1987).

Wheat et al.; "Diagnosis of Disseminated Histoplasmosis by Detection of *Histoplasma capsulatum* Antigen in Serum and Urine Specimens"; N. Engl. J. Med. 314:83–88 (1986).

Rao et al.; A Conformational Preference Parameter to Predict Helices in Integral Membrane Proteins; Biochem. Biophys. Acta 869:197–214 (1986).

Kaufman et al.; "Serodiagnosis of Fungal Diseases"; pp 446–466 In Rose, N.R., H. Friedman, and J. L. Fahey. Manual of Clin. Lab. Immunol. 3rd Edition. Amer. Soc. for Microbiology, Washington, D.C. (1986).

Hopp et al.; "Methods for Identifying Antigenic Determinants and Other Interaction Sites"; J. Immunol. Methods 88:1–18 (1986).

Kumar et al.; "Cross–reacting Human and Rabbit Antibodies to Antigens of *Histoplasma capsulatum, Candida albicans,* and *Saccharomyces cerevisiae*"; Infect. Immun. 48:806–812 (1985).

King, K.; "Histoplasmosis in Australia"; Med. J. Aust. 2:550–551 (1982).

Wheat et al.; "Immunoglobulin M and G Histoplasmal Antibody Response in Histoplasmosis"; Am. Rev. Resp. Dis. 128:65–70 (1983).

Kyte et al.; "A Simple Method for Displaying the Hydropathic Character of a Protein"; J. Mol. Biol. 157:105–132 (1982).

George et al.; "Radioimmunoassay: a Sensitive Screening Test for Histoplasmosis and Blastomycosis"; Am. Rev. Resp. Dis. 124:407–410 (1981).

McGinnis et al.; "Ajellomyces and its Synonym Emmonsiella"; Mycotaxon 8:157–164 (1979).

Goodwin et al.; "State of the Art Histoplasmosis"; Am. Rev. Resp. Dis. 117:929–956 (1978).

Chou et al.; "Prediction of the Secondary Structure of Proteins from their Amino Acid Sequence"; Adv. Enzymol. Relat. Areas Mol. Biol. 47:45–148 (1978).

Reiss et al.; "Solid–phase Competitive–binding Radioimmunoassay for Detecting antibody to the M Antigen of Histoplasmin"; J. Clin. Microbiol. 6:598–604 (1977).

Bauman et al.; "Comparison of Immunodiffusion and Complement Fixation Tests in the Diagnosis of Histoplasmosis"; J. Clin. Microbiol. 2:77–80 (1975).

Buechner et al.; "The Current Status of Serologic, Immunologic, and Skin Tests in the Diagnosis of Pulmonary Mycoses"; Chest 63:259–270 (1973).

Kwon–Chung et al., "*Emmonsiella capsulata:* Perfect State of *Histoplasma capsulatum*"; Science 177:368–369 (1972).

Ajello, J.; "Coccidioidomycosis and Histoplasmosis: a Review of their Epidemiology and Geographical Distribution"; Mycopathol. et Mycol. applicata 45:221–230 (1971).

Edwards et al.; "World–wide Pattern of Skin Sensitivity to Histoplasmin"; Am. J. Trop. Med. Hyg. 20:288–319 (1971).

Chandler et al.; "Immunology of the Mycoses. II. Characterization of the Immunoglobulin and Antibody Responses in Histoplasmosis"; J. Infect. Dis. 119:247–254 (1969).

* cited by examiner

Fig. 1

```
GH17        38 PPTTTTTTTTTTPTPTPTSIIPITP 62 (SEQ ID NO: 7)
               | •| | | | |||||||     ||
Cellulase  329 PTSTVTPTPTPTPTPTPTVTATPTP 353 (SEQ ID NO: 4)

GH17        38 PPTTTTTTTTTTPTPTPTSIIPITPIVPANKTIVLTTTIEP 78 (SEQ ID NO: 8)
               |||||||||||| | | |•  |||           ||| •|
PSA        183 PPTTTTTTTTTTTTTTTTKPPITTATTTKPPTTTTTTTTKP 223 (SEQ ID NO: 5)

GH17        22 TSGAAVDSCLLESNCPPPTTTTTTTTTTPTPTPTSIIPITPIVPANKTIVLTTTIEP 78 (SEQ ID NO: 9)
               |• |   •    •  |  ||||||||   | |||•  | |    |  |   |||  |
Xenopus    418 TTKATTTTPTTTTTTPTTTTTTTTTTKATTTTPTTTTPTTTTTKATTTTPTTTTTTP 474 (SEQ ID NO: 6)
```

DIAGNOSIS OF HISTOPLASMOSIS USING ANTIGENS SPECIFIC FOR H. CAPSULATUM

This application claims priority from U.S. Provisional Application Serial No. 60/043,332, filed Apr. 15, 1997, which is incorporated herein by reference.

BACKGROUND OF THE INVENTION

The present invention generally relates to methods of detection of a fungus and fungal infections through the use of protein antigens specific for the fungus. This invention also relates to methods for identifying such antigens, to antibodies raised against these antigens, to the use of such antigens and/or antibodies in assay methods for the determination of the presence of the fungus or diseases caused by the fungus in humans, other animals, plants, food, feed, and inorganic materials such as soil or air. The invention also relates to assay kits suitable for carrying out such diagnostic methods. In a preferred embodiment, the invention particularly relates to the fungus *Histoplasma capsulatum* (hereinafter *H. capsulatum*) and the infections caused by this fungus, histoplasmosis.

Rapid, positive detection of fungi has long been difficult because antibodies which are made to fungi are generally nonspecific. That is, these antibodies often cross-react with other fungi. This problem is thought to be due to the abundance of highly immunogenic carbohydrate antigenic determinants which are present, for example, in the fungal cell wall. The cross-reactive nature of fungal antigens is exemplified by previously known approaches to develop diagnostic methods to identify infections of *H. capsulatum. H. capsulatum* is a pathogenic dimorphic fungus that grows as multicellular mycelia in nature and as unicellular budding yeasts in humans and animals. Inhalation of airborne propagules results in a morphological transformation to the yeast form which causes pulmonary infection and occasional progressive disease, particularly in immunosuppressed patients. Histoplasmosis is highly endemic in the Ohio and Mississippi valleys in the United States, and it is also widely distributed in Latin America, southern Europe, Asia, Australia and Africa.

The diagnosis of histoplasmosis in humans is often suggested by results of a careful clinical evaluation and radiologic studies, but laboratory tests are necessary to confirm the diagnosis. Isolation of the organism from blood or tissue provides a definitive diagnosis. Serological tests are also important diagnostic tools for histoplasmosis. The most widely available tests are the immunodiffusion assay, which detects antibodies to heat-sensitive glycoproteins called H and M antigens, and the more sensitive complement fixation test, which is traditionally performed with yeast and mycelial antigens. More sensitive antibody assays such as radioimmunoassay and enzyme immunoassay have been used to detect IgM and IgG antibodies to crude fungal extracts. See, generally, references 39, 40, and 41.

Attempts to develop antibody serology tests for diagnosis of histoplasmosis have been hampered by poor specificity caused by immunologic cross-reactivity between various fungal species. The problem of cross-reactivity to other fungi may be worsened in the diagnosis of histoplasmosis by the fact that *H. capsulatum* is taxonomically closely related to two other pathogens, *Coccidioides immitis*, and *Blastomyces dermatitidis*. See Kwon-Chung, *Science* 177:368–369 (1972), and McGinnis et al., *Mycotaxon* 8:157–164 (1979). These fungi, which may be present along with *H. capsulatum*, cause coccidiomycosis and blastomycosis, diseases with etiologies similar to histoplasmosis. While *H. capsulatum, C. immitis*, and *B. dermatitidis* are known as imperfect fungi due to their rare or nonexistent sexual stage, studies have shown that *H. capsulatum* and *B. dermatitidis* are in the same telomorph genus, Ajellomyces, and those two fungi may be in the same taxonomic family as *C. immitis*, the Gymnoascaceae, order Onygenales, of the Ascomycetes. Another fungal pathogen, Candida sp., is also an ascomycete. See generally, Kwan-Chung et al., *Medical Mycology*, Lea and Febiger, Philadelphia (1992), which is incorporated by reference.

In view of the cross-reactivity and poor specificity common with fungal antibodies, there is a need for improved methods for identifying antigens which are specific to a target fungus. Such antigens are useful in diagnosis of diseases caused by the fungus and in determining the presence or absence of the fungus.

SUMMARY OF THE INVENTION

It is therefore an object of the invention to develop methods suitable for identifying protein antigens specific to a target fungus and, particularly, to *H. capsulatum.*

It is also an object to develop assays and assay reagents having improved specificity for identifying target fungal antigens and antibodies, and for the diagnosis of diseases caused by a target fungus and, particularly, by *H. capsulatum.*

Therefore, the present invention is directed to a method for identifying a protein antigen of a target fungus. A cDNA gene expression library is obtained for the target fungus, and the library is expressed to form an array of target-fungus proteins. Antisera to the target fungus and to a nontarget fungus are also obtained, each of which comprises antibodies to the target fungus and nontarget fungus, respectively. The nontarget fungus has at least one antigenic determinant (e.g. a protein determinant or glycoprotein determinant) in common (i.e., shared with) the target fungus. A protein antigen specific to the target fungus is then identified by identifying a target-fungus protein which is bound by the antibodies to the target fungus, but which is not substantially bound by antibodies to the nontarget fungus. That is, while antibodies to the target fungus are immunoreactive with the identified protein antigen, antibodies to the nontarget fungus are not substantially immunoreactive with the identified protein antigen.

The invention is also directed to substantially purified or isolated antibodies or antibody fragments. In one embodiment, the antibody or antibody fragment is immunoreactive with a protein antigen identified according to the aforementioned method. In another embodiment, the antibody or antibody fragment is immunoreactive with an antigen of *H. capsulatum*, but which is not substantially immunoreactive with antigens of each of *Coccidioides immitis, Blastomyces dermatitidis* or Candida sp. In a further embodiment, antibody or antibody fragment is immunoreactive with a protein antigen having the amino acid sequence set forth in SEQ ID NO: 3 or with a portion thereof that is specific to *H. capsulatum.*

The invention is directed, moreover, to a method for determining the presence or absence of a target-fungus antibody in a vertebrate such as a mammal. In one embodiment, the method comprises obtaining an antibody-containing sample from the vertebrate, contacting the sample with a target-fungus protein antigen, and determining whether an antibody in the sample immunoreacts with the target-fungus protein antigen. In an alternative embodiment directed to determining the presence or absence of antibodies to *H. capsulatum* in a mammal, the method comprises obtaining an antibody-containing sample from the mammal, contacting the sample with a protein antigen of *H. capsulatum* which is bound by antibodies to *H. capsulatum* but which is not substantially bound by antibodies to each of *Coccidioides immitis, Blastomyces dermatitidis* or Candida sp., and determining whether an antibody in the sample immunoreacts with the protein antigen of *H. capsulatum*. In an additional embodiment for determining antibodies to *H. capsulatum*, the method comprises obtaining an antibody-containing sample from the mammal, contacting the sample with a protein antigen having an amino acid sequence as set forth in SEQ ID NO: 3, and determining whether an antibody in the sample immunoreacts with the protein antigen.

The invention is further directed to a method for determining the presence or absence of a target-fungus protein antigen in a sample. The method generally comprises obtaining a sample to be tested for the presence or absence of the target-fungus protein antigen, contacting the sample with an antibody or antibody fragment which is immunoreactive with a target-fungus protein antigen, and determining whether the antibody or antibody fragment immunoreacts with the target-fungus protein antigen. As directed to determining the presence or absence of a *H. capsulatum* protein antigen in a mammal, the method comprises obtaining a sample to be tested for the presence or absence of the *H. capsulatum* protein antigen, contacting the sample with an antibody or antibody fragment which is immunoreactive with an antigen of *H. capsulatum*, but which is not substantially immunoreactive with antigens of each of *Coccidioides immitis, Blastomyces dermatitidis* or Candida sp., and determining whether the antibody or antibody fragment immunoreacts with the *H. capsulatum* protein antigen. In an alternative method for determining the presence or absence of a *H. capsulatum* protein antigen in a mammal, the method comprises obtaining a sample to be tested for the presence or absence of the *H. capsulatum* protein antigen, contacting the sample with an antibody or antibody fragment which is immunoreactive with a protein antigen having an amino acid sequence as set forth in SEQ ID NO: 3, and determining whether the antibody or antibody fragment immunoreacts with the protein antigen.

The invention is additionally directed to a kit that includes a reagent selected from, in one embodiment, one or more of the following: (i) a target-fungus protein antigen identified according to the aforementioned method, (ii) a fragment of a target-fungus protein antigen identified according to the aforementioned method wherein the fragment is bound by antibodies to the target fungus but is not substantially bound by antibodies to the nontarget fungus, and (iii) a target-fungus antibody or antibody fragment which immunoreacts with a target-fungus protein antigen identified according to the aforementiond method. In an alternative embodiment, the reagent is selected from one or more of the following: (i) a protein antigen of *H. capsulatum* which is bound by *H. capsulatum* antibodies but which is not substantially bound by antibodies to each of *Coccidioides immitis, Blastomyces dermatitidis* or Candida sp., (ii) a fragment of a *H. capsulatum* protein antigen wherein the fragment is bound by antibodies to *H. capsulatum* but is not substantially bound by antibodies to each of *Coccidioides immitis, Blastomyces dermatitidis* or Candida sp., and (iii) an antibody or antibody fragment which is immunoreactive with a *H. capsulatum* protein antigen but which is not substantially immunoreactive with antigens of each of *Coccidioides immitis, Blastomyces dermatitidis* or Candida sp. In yet another embodiment, the reagent is selected from: (i) a protein antigen having an amino acid sequence as set forth in SEQ ID NO:3, (ii) a protein antigen that includes a portion of the amino acid sequence as set forth in SEQ ID NO:3 wherein the included portion is bound by antibodies to *H. capsulatum* but is not substantially bound by antibodies to each of *Coccidioides immitis, Blastomyces* dermatitidis or Candida sp., (iii) an antibody or antibody fragment which is immunoreactive with a protein antigen having the amino acid sequence set forth in SEQ ID NO: 3, and (iv) an antibody or antibody fragment which is immunoreactive with a protein antigen that includes a portion of the amino acid sequence set forth in SEQ ID NO: 3 wherein the included portion is bound by antibodies to *H. capsulatum* but is not substantially bound by antibodies to each of *Coccidioides immitis, Blastomyces dermatitidis* or Candida sp. The kit also includes instructions for directing the use of the reagent for determining the presence or absence of the target fungus in a sample. In one embodiment, the instructions direct the use of the reagent for determining whether a mammal is presently infected or has been previously infected with the target fungus. In another embodiment in which the reagent is an antibody, the instructions direct the use of the antibody reagent for determining the presence or absence of an antigen in a nonvertebrate sample or environment, such as a plant, food, feed, feed component, air, water, or other fluid sample.

Other features, objects and advantages of the present invention will be in part apparent to those skilled in the art and in part pointed out hereinafter. All references cited in the instant specification are incorporated by reference. Moreover, as the patent and non-patent literature relating to the subject matter disclosed and/or claimed herein is substantial, many relevant references are available to a skilled aritsan that will provide further instruction with respect to such subject matter.

BRIEF DESCRIPTION OF THE DRAWINGS

FIG. 1 shows a comparison of the deduced amino acid sequence encoded by GH17 with threonine-rich regions of: (A) cellulase from the thermophilic bacterium *Caldocellum saccharolyticum* (SEQ ID NO: 4); (B), *Leishimania surface* antigen (SEQ ID NO: 5); and (C), integumentary mucin from *Xenopus laevis* (SEQ ID NO: 6) using the NCBI BLAST analysis program. Identical residues are indicated with a (|), and conserved residues are marked with a (·)

FIG. 4 shows the results of an immunoblot analysis of the immunoreactivity and specificity of the β-galactosidase fusion protein of the recombinant clone GH17. The immunoreactive fusion protein band is indicated by an arrow.

FIG. 5 shows an SDS-PAGE and immunoblot analysis of expression of GH17-his in pPROEX-1™ protein expression vector.

In FIG. 5A, 10% SDS-PAGE was loaded with *E. coli* extract without IPTG induction (lane 1), and after IPTG induction for 3 hr (lane 2). The immunoblots were developed with human histoplasmosis serum pool (1:500), enzyme-labeled anti-human IgG secondary antibody, and substrate.

DETAILED DESCRIPTION OF THE PREFERRED EMBODIMENTS

Figure 2:
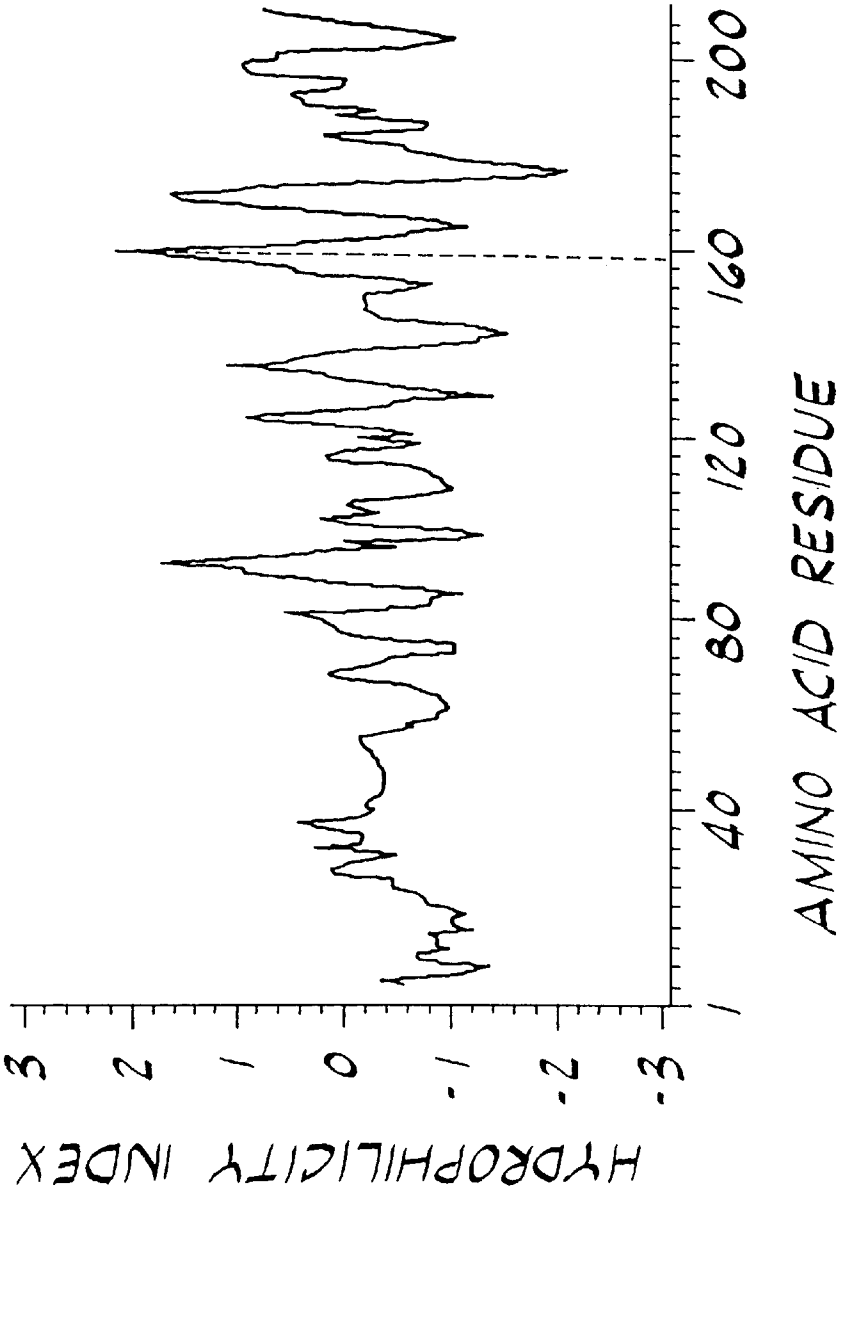
FIG. 2 shows a hydropathy plot of the protein encoded by GH17. Hydropathy analysis was performed by the method of Hopp and Woods. Hydropathy values were averaged for a window of six amino acid residues. Positive numbers indicate hydrophilicity. The point of highest hydrophilicity (Average hydrophilicity=2.08, between residues 155–160) is marked with a broken vertical line.

The present invention is directed toward protein antigens which are specific to a target fungus, to methods of obtaining such antigens, to antibodies to such antigens, and to assays employing such antigens and antibodies.

An antigen specific to a particular target fungus is identified by a) obtaining a cDNA gene expression library for the target fungus, b) expressing target fungal proteins from the cDNA gene expression library, c) obtaining antisera to the target fungus which has antibodies to the target fungus, d) obtaining antisera to the nontarget fungus which has antibodies to the nontarget fungus and e) identifying a target-fungus protein which is bound by the antibodies to the target fungus, but which is not substantially bound by the antibodies to the nontarget fungus.

The steps of the above method need not be performed in any particular order. In a preferred embodiment of the above method, the cDNA expression library is first screened with an antisera to the target fungus. Clones which are highly reactive to the target fungus are thus identified, and these selected clones are then screened with antisera to the nontarget fungus. The clones which produce a protein which is bound by antibodies in the antisera to the target fungus but not by antibodies in the antisera to other microorganisms (e.g. nontarget fungi) are then identified. Various manipulations known in the art can utilize these clones to produce and substantially purify the protein antigens encoded by the clones. The protein antigens can then be used as discussed below.

The procedures disclosed herein which involve the molecular manipulation of nucleic acids are known to those skilled in the art. See generally Fredrick M. Ausubel et al. (1995), "Short Protocols in Molecular Biology", John Wiley and Sons, and Joseph Sambrook et al. (1989), "Molecular Cloning, A Laboratory Manual", second ed., Cold Spring Harbor Laboratory Press.

A used herein, the term "target fungus" (pl. "target fungi") denotes any fungus for which there is a particular interest. Examples of target fungi are fungi which are pathogens of animals or plants, allergens, food spoiling agents, or food sources. Preferred target fungi include Ascomycetes. More preferred target fungi are those fungi in the genus Gymnoascaceae. Even more preferred fungi are those in the genus Ajellomyces, and the most preferred target fungus is *H. capsulatum*. A "nontarget fungus" may be any fungus that is desired to be distinguished from the target fungus, for identification or diagnostic purposes, by an immunoassay. In general, the nontarget fungus includes at least one antigenic determinant in common with the target fungus. As such, the nontarget fungus can cross react with an antibody that recognizes this shared antigenic determinant. Exemplary nontarget fungi may be selected from fungi known to cause a disease with similar symptoms as the target fungus.

The cDNA gene expression library of the target fungus may be obtained from a commercial source or prepared by methods known in the art, using an appropriate morphological stage of the target fungus. An easily culturable stage such as mycelium is preferred. Common vectors used for this purpose are plasmid, bacteriophage, and mammalian cells. A preferred expression library is one utilizing a phage such as bacteriophage λgt11, with poly(A)+mRNA.

The target fungus proteins are expressed by any method known in the art. For the preferred λgt11 expression library, the proteins are generally expressed by induction with IPTG.

Antisera to the target fungus may be obtained in any manner known in the art. Preferably such antisera are obtained by preparing an antigen which will, upon immunization of an animal with the fungus, yield an antisera which contains a population of antibodies which, in sum, will immunoreact to many antigens of the target fungus. An unfractionated preparation of the target fungus is thus a preferred antigen preparation. However, a fractionated preparation could also be employed. When the target fungus is pathogenic to vertebrates which are capable of mounting an immunological response to the fungus, the preferred screening antisera is serum from infected individuals. A more preferred screening antisera is pooled serum from several infected individuals. Antisera to the nontarget fungus can be obtained by methods similar to the methods used to prepare antisera to the target fungus.

Target-fungal proteins which are bound by the target-fungus antibodies but which are not substantially bound by the nontarget-fungus antibodies can be identified by screening each of the antisera by appropriate immunological assays known in the art. The terms "immunoreact", "bind", "are bound to" or grammatical derivations thereof are used interchangeably herein, and refer to the capability of an antibody or an antibody fragment to specifically attach to an antigen at the antibody's Fab binding site. Exemplary screening assays include precipitin assays and label-based assays. Preferably, the antigen is identified from the expressed cDNA gene expression library by blotting the expressed proteins (e.g. from phage plaques) onto membranes then screening the membranes with the antisera made to each fungus.

The degree of immunological cross-reactivity for the identified target-fungus protein (generally referred to herein as a target-fungus specific antigen) is preferably sufficiently low so that tests that detect the antigen or antibodies to the antigen are useful for reliably distinguishing the fungus from nontarget fungi. The degree of immunological cross-reactivity with nontarget fungi and/or other microorganisms of interest, when assessed by immunoassay (for example Western blot or ELISA), is preferably less than about 10%, more preferably less than about 5%, still more preferably less than about 2%, even more preferably less than about 1%, and most preferably less than about 0.1%.

The identified target-fungus specific protein antigen is more specifically characterized as follows, with the various aspects defining the protein to be considered both independently and in combination. The target fungus-specific protein antigen is preferably substantially free from non-protein determinants such as carbohydrates, phosphorylcholine, and/or other moieties which, when attached to or otherwise associated with the protein, would reduce the immunological specificity of the protein.

The term "specific" is used herein to denote an antigen which is not present in nontarget fungi. When referring to an antibody or to an assay, "specific" denotes a substantial lack of cross-reactivity with nontarget fungi. As an example, an antigen of a target fungus which infects mammals would be specific if antibodies in serum produced by a target fungus-infected vertebrate bound to the antigen, but sera produced in vertebrates which are infected with a nontarget fungus do not substantially cross-react with the antigen. The extent of cross-reactivity can be more specifically characterized with regard to a set (i.e. group or population) of samples being evaluated. In a sample population known to comprise the target-fungus antigen or antibodies to the antigen, the presence of the antigen or antibody is correctly determined in preferably at least about 90% of the samples, more preferably in at least about 95% of the samples and most preferably in at least about 99% of the samples. Conversely, in a sample population known to both (i) lack the target fungus antigens or antibodies thereto and (ii) comprise a nontarget fungus antigen or antibodies thereto, the absence of the target fungus antigen or antibody thereto is correctly determined in preferably at least about 90% of the samples, more preferably in at least about 95% of the samples and most preferably in at least about 99% of the samples. As another example, an antigen on a plant pathogenic fungus is specific if antisera made to that antigen does not substantially cross-react with antigens on other nontarget fungi which might be present in the same environment as the plant pathogenic fungus.

Target-fungus specific protein antigens with such cross-reactivity can be varied from the identified protein antigen, but will preferably have an amino acid sequence which has a sequence identity or, alternatively, a homology of at least about 75%, more preferably at least about 90%, even more preferably at least about 95% and most preferably at least about 98% relative to the amino acid sequence of the identified protein antigen or, alternatively, as encoded by the cDNA clone thereof.

In a preferred embodiment the target fungus is H. capsulatum. Preferred nontarget fungi are *C. immitis, B. dermatitidis*, and Candida sp. *H. capsulatum* proteins expressed from a cDNA expression library are screened, preferably by immunoblot, against antisera to *H. capsulatum* and at least one of the nontarget fungi. The antisera are preferably provided by pooled sera from individuals infected with the target and nontarget fungi. Where the target fungus is *H. capsulatum*, a preferred protein antigen has the amino acid sequence set forth as SEQ ID NO:3. (See example). In another embodiment, the protein is a *H. capsulatum*-specific protein antigen and has an amino acid sequence which includes at least a portion of the amino acid sequence set forth as SEQ ID NO:3 which is specific for *H. capsulatum*, the included portion being, in a preferred protein, at least 5 amino acids in length. The *H. capsulatum*-specific antigen identified in this manner is not substantially cross-reactive with antisera to the nontarget fungus. (See Example).

The target-fungus specific antigen, identified for example by the afore-described screening protocols, can be isolated and produced in substantially purified form according to methods known in the art. Briefly, the cDNA clone corresponding to the identified target-fungus specific antigen, or more generally any nucleic acid polymer encoding the target-fungus specific protein antigen, can be incorporated into an expression vector for recombinant production of the protein antigen, as discussed below.

The nucleic acid polymer can have the cDNA nucleotide sequence of the isolated cDNA clone. The nucleic acid polymer can, alternatively, have a mRNA nucleotide sequence corresponding to the cDNA sequence. Where the target fungus is *H. capsulatum*, the nucleic acid polymer preferably has the cDNA nucleotide sequence set forth as SEQ ID NO:2 or a mRNA nucleotide sequence corresponding to the sequence set forth as SEQ ID NO:2.

In an additional embodiment, the nucleic acid polymer can encode a fungus-specific protein antigen and have an nucleotide sequence which includes at least a portion of the nucleotide sequence of the isolated cDNA, the included portion being at least 15 base pairs in length. In a further embodiment, the nucleic acid polymer can be at least 15 base pairs in length and encode a fungus-specific protein antigen having an amino acid sequence which has a sequence identity or, alternatively, a homology of at least about 75%, more preferably at least about 90%, even more preferably at least about 95% and most preferably at least about 98% relative to the amino acid sequence encoded by the isolated cDNA.

The above-disclosed nucleic acid polymer which encodes a fungus-specific protein antigen is preferably used to create a vector which is used, for example, to replicate or translate the nucleic acid polymer. Translation of the nucleic acid polymer is preferably accomplished by an expression vector by methods known in the art. The expression vector can be, for example, a hybrid plasmid, a virus, or other nucleic-acid-polymer construct which is suitable for use in expressing the antigen in a eukaryotic or prokaryotic host-cell, in vitro, according to methods known in the art. In the case of *H. capsulatum*, preferred expression vectors are λgt11 and the pProEXm-1 protein expression system, which produces a fusion protein containing 6 histidines.

A host cell can be transformed with the above-disclosed vector for recombinant production of the target fungus-specific protein antigen. The host cell can be, for example, a bacterial host cell such as *E. coli*, a yeast cell, a mammalian cell, or any other suitable host cell in which the antigen can be expressed and from which the antigen can be substantially isolated and purified.

The isolated fungus-specific protein antigen can be utilized to produce an antibody specific for the antigen. The antigenic protein or fragment against which the antibody is raised and to which the antibody binds is preferably substantially purified, and is further characterized as set forth above, with the various aspects defining the protein antigen to be considered both independently and in combination.

The antibody may be a mono-specific antibody. The monospecific antibody may be a monoclonal antibody produced, for example, by the method of Galfre et al., *Nature* 266:550 (1977). Alternatively, the monospecific antibody may be a recombinant antibody produced, for example, by the method of Lowman et al, *Biochemistry* 30:10832–10838 (1991).

The antibody can also be a polyclonal antibody. The polyclonal antibody can be prepared by immunizing a mammal such as a mouse or rabbit with the fungus-specific antigen and subsequently isolating the serum therefrom to obtain an antiserum that contains the polyclonal antibodies. If the fungus is a pathogen of a vertebrate animal, such as *H. capsulatum*, polyclonal antibodies reactive to the specific antigen are generally produced in the serum of an infected animal. That serum may be collected and utilized as a polyclonal antiserum to the fungus.

The target fungus-specific antigen, and antibodies made to that specific antigen can be utilized in assays to determine the presence or absence, in a sample, of antigens or antibodies which are indicative of or diagnostic for the target fungus.

Any portion of the antigen which is specific for the fungus may be utilized for identifying the target fungus in a sample, and specific peptide sequences as small as five amino acids in length may be easily obtained by methods known in the art. These specific fragments may, for example, be used alone or they may be engineered by methods known in the art to be part of a fusion protein, preferably comprising two domains, a first domain that includes at least a portion of the amino acid sequence encoded by the nucleic acid polymer, the included portion being at least 5 amino acids in length, and a second domain that includes the amino acid sequence of another protein or polypeptide. In a preferred embodiment, the second domain includes the amino acid sequence of a protein from the expression vector, such as β-galactosidase or other protein incorporated in an expression system, which may facilitate expression and/or subsequent purification of the expressed antigen from the host-cell lysate.

In the case of a fungus disease of humans and other animals, the tests will preferably allow one to distinguish the fungal disease from other clinical conditions, especially from other fungal infections. Without being bound to a particular theory not specifically required in the claims, the target-fungus specific antigens result from the above-disclosed method because the expressed proteins from the cDNA expression library do not contain carbohydrate moieties which would be present in fungal antigen preparations prepared by prior art methods. Prior art methods of immunizing vertebrates with components of the target fungus generally failed to identify specific antigens because the immune system of the immunized vertebrate would mount an immune response to the antigenic carbohydrate moieties of the immunogen target fungus. However, the carbohydrate moieties of the immunogen target fungus are often also present in the nontarget fungi, thus leading to cross-reactivities with the nontarget fungi. In particular, fungi which are closely related taxonomically, such as *H. capsulatum* and *B. dennatitidis*, generally have more antigenic determinants in common than fungi which are less closely related, such as *H. capsulatum* and *Agaricus bisporus*, the common cultivated mushroom. As such, the present method is particularly suited for developing immunoassays for target fungi which might be confused for closely related nontarget fungi.

In the preferred embodiment, a test for histoplasmosis developed with an antigen specific for *H. capsulatum* (as in the Example) allows a determination of the presence or absence of antibodies to *H. capsulatum* which do not immunoreact with nontarget fungi present in the sample—particularly *Coccidioides immitis, Blastomyces dermatiditis*, and/or Candida species. Thus, the invention as applied to *H. capsulatum* provides diagnostic methods (i.e., assays) for determining whether a mammal has been infected with *H. capsulatum*. These methods, combined with clinical observations and findings based on known and/or on later-developed techniques, facilitate diagnosis of histoplasmosis.

One embodiment of the assay method as applied to a target fungus is referred to herein as an antibody assay. This method comprises detecting the presence or absence of antibodies to a target fungus-specific antigen in a sample obtained from a vertebrate. The presence or absence of the target fungus-specific antibodies are detected by contacting the sample with an antigen specific to the target fungus and determining whether the sample contains antibodies that bind to the target fungus-specific antigen. The preferred antigen is further characterized as set forth above, with the various aspects defining the antigen to be considered both independently and in combination. Exemplary antibody assays, discussed in more detail below, include precipitin-based immunoassays, indirect label-based immunoassays, direct label-based immunoassays and inhibition/competitive-type label-based immunoassays. The presence of target fungus-specific antibodies in a sample obtained from the mammal is evidence of current and/or past exposure or infection with the target fungus. In an alternative embodiment, referred to herein as an antigen assay, the method comprises detecting the presence or absence of antigens specific to the target fungus in a sample. The presence or absence of target fungus-specific antigens is detected by contacting the sample with an antibody capable of binding to a target fungus-specific antigen and determining whether the antibody binds to the target fungus-specific antigen. The preferred target fungus-specific antibody is as set forth above, with the various aspects defining the antibody to be considered both independently and in combination. The target fungus-specific antigen being detected is further characterized as set forth above, with the various aspects defining the antigen to be considered both independently and in combination. Exemplary antigen assays, discussed in more detail below, include precipitin-based immunoassays, indirect label-based immunoassays, direct label-based immunoassays and inhibition/competitive-type label-based immunoassays. The presence of antigens specific to the target fungus in a sample is evidence of the presence of the target fungus in the sample.

As applied to *H. capsulatum*, the detection of antibodies which bind to the *H. capsulatum*-specific antigen in a sample from a mammal is evidence of past or current infection with *H. capsulatum*. Similarly, the detection of *H. capsulatum*-specific antigens in a sample from a mammal is strong evidence of current infection with *H. capsulatum.*

The following additional concerns are applicable to either of the aforementioned antibody assay or antigen assay as applied to a target fungus such as *H. capsulatum*. The mammals from which a sample is obtained are preferably humans, domestic livestock and/or pets which are suspected of being or known to be susceptible to fungal infection by the target fungus (e.g. *H. capsulatum*). The sample can be a blood sample, a plasma sample, a serum sample, a urine sample, a sputum sample, a saliva sample or any other biological sample obtained from the mammal which is suspected of potentially having antibodies to the target fungus (e.g. *H. capsulatum*) or having target-fungus (e.g. *H. capsulatum*) antigens.

The sample can be pretreated prior to testing the sample in the assay. Exemplary pretreatment steps can include concentrating the sample and/or eliminating interfering substances (e.g. acid in urine or rheumatoid factors in serum). Other pretreatment steps will be apparent to a person of skill in the art. Moreover, additionally or alternatively to detecting whether antigen-antibody binding occurs in either of the aforementioned general methods, the extent of such binding can be quantitatively determined using methods known in the art.

The antibody assays of the present invention can be more specifically characterized according to a variety of formats set forth below and/or known in the art. One approach includes the use of precipitin-based immunoassays. For example, the presence or absence of the antibodies can be detected by layering a first solution including the target fungus-specific antigen over the undiluted (i.e., neat) sample or over a second solution including the sample, the layered solution typically being formed in a container such as a test-tube, and observing the layered solution for the formation or the lack of formation of a precipitate comprising bound antigen and antibody. The amount of target fungus-specific antigen in the first solution is preferably an amount which is necessary, on average, to form a precipitate with samples drawn from a vertebrate known to contain antibodies to the target fungus. The steps of this approach can, alternatively, be repeated, in parallel or in series, using various amounts of the target fungus-specific antigen in the first solution, with the amount of antigen in the solution varying over a range which includes an amount which is about, on average, necessary to form a precipitate with samples drawn from mammals known to have histoplasmosis. Precipitin-based immunoassays can also be carried out in gels such as agar or polyacrylamide gels or their equivalents known in the art, by methods typically referred to as immunodiffusion, immunoelectrophoresis, counterimmunoelectrophoresis and/or rocket electrophoresis, among others. For example, the presence or absence of the antibodies are detected by placing a first solution including the target fungus-specific antigen in a gel or in a well adjacent to a gel, placing the undiluted sample or a second solution including the sample, in a gel or in a well adjacent to a gel, allowing the target fungus-specific antigen and antibodies to diffuse in the gel, and observing the gel for the formation or the lack of formation of a precipitate comprising bound antigen and antibody. Turbidometric or nephelometric-type assay formats can also be employed. Precipitin-based immunoassays offer the advantage of not requiring a solid-phase matrix, and as such, may be suited for particular applications known in the art (e.g. automated systems).

Another approach for the antibody assay of the present invention includes the use of label-based assay techniques, including direct, indirect and/or inhibition/competitive radioimmunoassays, enzyme-linked immunoabsorbant assays (ELISA), immunofluorescent assays, immunochromatographic assays, and other techniques known in the art. For example, the presence or absence of the antibodies can be detected using an indirect label-based immunoassay by immobilizing the target fungus-specific antigen on a solid-phase, contacting the immobilized antigen with the undiluted sample or with a solution including the sample to allow any target fungus-specific antibody which may be present in the sample to specifically bind to the immobilized antigen, thereby forming a first immobilized complex which includes either solid-phase/target fungus-specific antigen or solid-phase/target fungus-specific antigen/antibody depending on whether the target fungus-specific antibody was present in the sample, washing the first immobilized complex to remove any unbound target fungus antibody and/or other serum components, contacting the first immobilized complex with a detectable secondary antibody capable of binding to the target fungus-specific antibody, thereby forming a second immobilized complex which includes either solid-phase/target fungus-specific antigen or solid-phase/target fungus-specific antigen/antibody/secondary-antibody depending on whether target fungus antibody was present in the sample, washing the second immobilized complex to remove any unbound secondary antibody, and detecting the presence or absence of the secondary antibody on the second immobilized complex. The detectable secondary antibody can be labeled according to methods known in the art or later developed. For example, the secondary antibody can be a radiolabeled antibody (e.g. an antibody labeled with a gamma-emitting $^{1251}$I isotope) which is detected by radiographic methods or with instruments such as counters which measure the level of radioactivity present. The secondary antibody can also be an enzyme-conjugated antibody (e.g. an antibody conjugated with alkaline phosphatase, horseradish peroxidase, or other enzyme) which is detected by contacting the enzyme-conjugated antibody with a color-producing enzyme substrate. The secondary antibody can alternatively be tagged with biotin (or an equivalent) or with a fluorochrome (e.g. fluorescein and rhodamine) or a dye or other colored substance (e.g. colloidal gold) which can be detected visually or by known spectroscopic methods.

In another example of an indirect label-based immunoassay, the presence or absence of target fungus-specific antibodies can be detected using a Western blot format. This method is particularly advantageous in that it includes a step for separating the target fungus-specific antigen from other proteins in the sample in which it is present (e.g. for isolating recombinantly-produced target fungus-specific antigen present in a host-cell lysate). This method includes electrophoretically separating a target fungus-specific protein antigen electrophoretically, transferring the separated protein antigen to a solid-phase membrane (e.g. a nitrocellulose or nylon membrane), contacting the solid-phase/target fungus-specific antigen complex with an undiluted sample or with a solution including the sample to allow any target fungus-specific antibody which may be present in the sample to bind to the antigen, and to form a first complex which includes either solid-phase/target fungus-specific antigen or solid-phase/target fungus-specific antigen/antibody, depending on whether antibody was present in the sample, washing the first complex to remove any unbound antibody, contacting the first complex with a detectable secondary antibody capable of binding to the solid phase-bound antibody, thereby forming a second immobilized complex which includes either solid-phase/target fungus-specific antigen or solid-phase/target fungus-specific antigen/antibody/secondary-antibody depending on whether target fungus-specific antibody was present in the sample, washing the second immobilized complex to remove any unbound secondary antibody, and detecting the presence or absence of the secondary antibody on the second immobilized complex. The detectable secondary antibody can, for example, be radiolabeled, enzyme- conjugated, tagged with a fluorochrome, or dyed as described above.

The presence or absence of target fungus-specific antibodies can, in another exemplary method, be detected using a direct label-based immunoassay. This method includes immobilizing a first anti-immunoglobulin antibody (e.g. IgG) capable of binding to the target fungus antibody being detected on a solid-phase (e.g. beads, membrane, matrix, etc.), contacting the immobilized anti-immunoglobulin antibody with an undiluted sample or with a solution including the sample to form a first complex which includes either solid-phase/anti-immunoglobulin-antibody or solid-phase/anti-immunoglobulin-antibody/target fungus-specific antibody, depending on whether target fungus-specific antibody was present in the sample, washing the first complex, contacting the first complex with a labeled target fungus-specific antigen to allow any target fungus-specific antibody present in the first complex to bind to the target fungus-specific antigen and to form a second complex comprising either solid-phase/anti-immunoglobulin-antibody or solid-phase/anti-immunoglobulin-antibody/target fungus-specific antibody/target fungus-specific antigen, depending on whether target fungus-specific antibody was present in the sample, washing the second complex to remove any unbound labeled target fungus-specific antigen, and detecting whether the labeled target fungus-specific antigen is present or absent in the second complex. The target fungus-specific antigen can be labeled according to methods now known in the art or later developed, including, for example, being radiolabeled, enzyme-conjugated, tagged with a fluorochrome, dyed or otherwise associated with a colored material, as described above.

The presence or absence of target fungus-specific antibodies can, in a further exemplary method, be detected using a inhibition/competitive label-based immunoassays. This method includes establishing a baseline reading for a control assay by immobilizing a target fungus-specific antigen on a solid-phase, contacting the immobilized target fungus-specific antigen with a detectable (e.g. labeled) target fungus-specific antibody to form a control complex including solid-phase/target fungus-specific-antibody/detectable target fungus-specific antibody, washing the control complex to remove any unbound detectable target fungus-specific antibody therefrom, and detecting the baseline level of target fungus-specific antibody bound to the immobilized target fungus-specific antigen on the control complex. The method further includes, in a separate, independent test assay, immobilizing a target fungus-specific antigen on a solid-phase, contacting the immobilized target fungus-specific antigen with both (1) a detectable (e.g. labeled) target fungus-specific antibody and (2) an undiluted sample or with a solution including the sample to allow any target fungus-specific antibody which may be present in the sample to bind to at least some of the immobilized target fungus-specific antigen and to thereby form a test complex in which at least some of the bound detectable target fungus-specific antibody may have been competitively inhibited from binding to the immobilized target fungus-specific antigen, depending on whether target fungus-specific antibody was present in the sample, washing the test complex to remove any unbound target fungus-specific antibody, detecting the level of detectable-target fungus-specific antibody bound to the test complex, and comparing the level of detectable-target fungus-specific antibody bound to the test complex to the baseline level of detectable target fungus-specific antibody bound to the control complex, a decrease in such level indicating the presence of target fungus-specific antibody in the sample. The detectable target fungus-specific antibody can, for example, be radiolabeled, enzyme-conjugated, tagged with a fluorochrome, dyed or otherwise associated with a colored material as described above.

The approaches set forth above for determining the presence or absence of antibodies to target fungus-specific antibody in a sample are to be considered exemplary and non-limiting of the many formats known in the art by which a sample suspected of including antibodies is contacted with an antigen and the presence or absence and/or quantitative extent of antigen-antibody binding is determined. Moreover, the exact sequence of steps is not narrowly critical and can be varied as is appropriate in the art. Certain steps may be omitted altogether and/or combined with other steps. For example, the sample and-labeled antigen can, in some assay formats, be added together. As another example, assays may not require a washing step to remove unbound antibodies. Assays such as immunochromatographic assays where reactants flow across and/or through the solid phase are exemplary. Certain additional steps may also be added, in series and/or in parallel combination, to the aforementioned steps, as appropriate in the art. For example, the assays can optionally include one or more blocking steps or proteins or detergents in the diluent to decrease the non-specific binding of antibodies, primary or secondary, to the solid-phase. The assays of the invention can also be automated, with appropriate modifications to the described steps. All of the above antibody assays are effective in detecting target fungus-specific antibodies for any fungus, including *H. capsulatum*, which is capable of eliciting an antibody response in a vertebrate.

The antigen assays of the present invention are useful in any situation where a determination of the presence or absence of a target fungus is desired. Examples include the determination of the presence of a target fungus in an animal or plant suspected of being infected with the target fungus, in a food or feed suspected of being contaminated with the target fungus, in inorganic materials such as soil or air for the determination of the presence of an allergenic or pathogenic target fungus, and for the identification of a specific target fungus where the identity of the fungus is unknown.

The antigen assays of the present invention can be more specifically characterized according to a variety of formats set forth below and/or known in the art. One approach includes the use of precipitin-based immunoassays. For example, the presence or absence of the target fungus-specific antigens in the sample can be detected by layering a first solution including the target fungus-specific antibody over the undiluted sample or over a second solution including the sample, the layered solution typically being formed in a container such as a test-tube, and observing the layered solution for the formation or the lack of formation of a precipitate comprising bound antigen and antibody. The amount of target fungus-specific antibody in the first solution is preferably an amount which is necessary, on average, to form a precipitate with samples previously known to comprise the target fungus. The steps of this approach can, alternatively, be repeated, in parallel or in series, using various amounts of the target fungus-specific antibody in the first solution, with the amount of antibody in the solution varying over a range which includes an amount which is about, on average, necessary to form a precipitate with samples previously known to contain the target fungus-specific antigen. Precipitin-based immunoassays can also be carried out in gels such as agar or polyacrylamide gels or their equivalents known in the art, by methods typically referred to as immunodiffusion, immunoelectrophoresis, counterimmunoelectrophoresis and/or rocket electrophoresis, among others. For example, the presence or absence of the antigens are detected by placing a first solution including the target fungus-specific antibody in a gel or in a well adjacent to a gel, placing the undiluted sample or a second solution including the sample, in a gel or in a well adjacent to a gel, allowing the target fungus-specific antibody and antigens to diffuse within the gel and observing the gel for the formation or the lack of formation of a precipitate comprising bound antigen and antibody.

Another approach for the antigen assay of the present invention includes the use of label-based assay techniques, including direct, indirect and/or inhibition/competitive radioimmunoassays, enzyme-linked immunoabsorbant assays (ELISA), immunofluorescent assays, immunochromatographic assays, and other techniques known in the art. For example, the presence or absence of the antigens can be detected in a direct sandwich-type format by immobilizing target fungus-specific antibody on a solid-phase, contacting the immobilized antibody with an undiluted sample or with a solution including the sample to allow any target fungus-specific antigen which may be present in the sample to bind to the immobilized antibody, thereby forming a first immobilized complex which includes either solid-phase/target fungus-specific antibody or solid-phase/target fungus-specific antibody/target fungus-specific antigen, depending on whether the target fungus-specific antigen was present in the sample, washing the first immobilized complex to remove any unbound target fungus-specific antigen, contacting the complex with a detectable secondary antibody capable of binding to a different epitope on the target fungus-specific antigen, thereby forming a second immobilized complex which includes either solid-phase/target fungus-specific antibody or solid-phase/target fungus-specific antibody/target fungus-specific antigen/secondary-antibody, depending on whether target fungus-specific antigen was present in the sample, washing the second immobilized complex to remove any unbound secondary antibody, and detecting the presence or absence of the secondary antibody on the second immobilized complex. The secondary antibody can, for example, be radiolabeled, enzyme-conjugated, tagged with a fluorochrome or dyed as described above.

In another example of an indirect label-based immunoassay, the presence or absence of target fungus-specific antigen can be detected using a Western blot format. This method includes electrophoretically separating proteins contained in the sample in a gel (e.g. such as a polyacrylamide gel), electrophoretically transferring the separated proteins to a solid-phase membrane (e.g. a nitrocellulose membrane), contacting the separated proteins with an unlabeled target fungus-specific antibody to allow any target fungus-specific antigen which may have been present in the sample to bind to the antibody and form a first complex with includes either solid-phase/target fungus-specific antigen or solid-phase/target fungus-specific antigen/target fungus-specific antibody, depending on whether target fungus-specific antigen was present in the sample, washing the first complex to remove unbound target fungus-specific antibody, contacting the first complex with a detectable secondary antibody to form second complex which includes either solid-phase/target fungus-specific antigen or solid-phase/target fungus-specific antigen/target fungus-specific antibody/secondary-antibody, depending on whether target fungus-specific antigen was present in the sample, and detecting the presence or absence of the secondary antibody bound to the antigen in the second complex. The secondary antibody can, for example, be radiolabeled, enzyme-conjugated, tagged with biotin or an equivalent thereto, a fluorochrome, dyed or otherwise associated with a colored material as described above.

In an exemplary direct Western blot immunoassay, the presence or absence of the antigens in the sample can be detected using a method which includes electrophoretically separating proteins contained in the sample in a gel (e.g. such as a polyacrylamide gel), transferring the separated proteins to a solid-phase membrane (e.g. a nitrocellulose or nylon membrane), contacting the transferred proteins with a detectable target fungus-specific antibody to allow any target fungus-specific antigen which may have been present in the sample to bind to the target fungus-specific antibody and form a complex which includes either gel/target fungus-specific antigen or gel/target fungus-specific antigen/target fungus-specific antibody, washing any unbound target fungus-specific antibody away from the gel and detecting the presence or absence of labeled target fungus-specific antibody bound to the antigen in the gel. The target fungus-specific antibody can, for example, be radiolabeled, enzyme-conjugated, tagged with a fluorochrome or dyed, as described above.

Alternatively, the presence or absence of the antigens in a sample can be detected in an inhibition/competitive-type format by mixing a solution including a detectable (e.g. labeled) target fungus-specific antibody with the undiluted sample or with a solution including the sample to allow any target fungus-specific antigen which may be present in the sample to bind with the detectable target fungus-specific antibody and to form a test solution which includes either unbound detectable target fungus-specific antibody or a detectable target fungus-specific antibody/target fungus-specific antigen complex depending on whether target fungus-specific antigen was present in the sample. The method further includes immobilizing a target fungus-specific antigen on a solid-phase, contacting the immobilized target fungus-specific antigen with the test solution to allow any unbound detectable target fungus-specific antibody present in the test solution to bind with the immobilized target fungus-specific antigen and form an immobilized complex including solid-phase/target fungus-specific antigen or solid-phase/target fungus-specific antigen/detectable target fungus-specific antibody depending on whether target fungus-specific antigen was present in the sample, washing the solid-phase to remove any unbound target fungus-specific antibody, and measuring the presence or absence of the detectable target fungus-specific antibody on the immobilized complex. The detectable antibody can be radiolabeled, enzyme-conjugated, tagged with a fluorochrome or dyed, as described above. In an alternative variation on this type of format, an antigen assay can include immobilizing a target fungus-specific antibody on a solid-phase, contacting the immobilized antibody with both (1) a detectable (e.g. labeled) target fungus-specific antigen and (2) an undiluted sample or a solution including the sample to allow any target fungus-specific antigen which may be present in the sample to bind to at least some of the immobilized target fungus-specific antibody and to thereby form a test complex in which at least some of the detectable target fungus-specific antigen may have been competitively inhibited from binding to the immobilized target fungus-specific antibody, depending on whether target fungus-specific antigen was present in the sample, washing the test complex to remove any unbound target fungus-specific antigen, and detecting the level of detectable target fungus-specific antigen bound to the test complex. If desired, the level of detectable target fungus-specific antigen bound to the test complex can be compared to a baseline level of detectable target fungus-specific antigen bound to a control complex, with a decrease in such level indicating the presence of target fungus-specific antigen in the sample. The detectable target fungus-specific antigen can, for example, be radiolabeled, enzyme-conjugated, tagged with biotin or an equivalent thereto, a fluorochrome, dyed or otherwise associated with a colored material as described above.

The approaches set forth above for determining the presence or absence of target fungus-specific antigens in a sample are to be considered exemplary and non-limiting of the many formats known in the art by which a sample suspected of including antigens is contacted with an antibody and the presence or absence and/or quantitative extent of antigen-antibody binding is determined. Moreover, the exact sequence of steps is not narrowly critical and can be varied as is appropriate in the art. Certain steps may be omitted altogether and/or combined with other steps. For example, the sample and labeled antigen can, in some assay formats, be added together. As another example, assays may not require a washing step to remove unbound antibodies. Assays such as immunochromatographic assays where reactants flow across and/or through the solid phase are exemplary. Certain additional steps may also be added, in series and/or in parallel combination, to the aforementioned steps, as appropriate in the art. For example, the assays can optionally include one or more blocking steps to decrease the non-specific binding of antibodies, primary or secondary, to the solid-phase. The assays of the invention can also be automated, with appropriate modifications to the described steps. All of the above antigen assays are effective in detecting target fungus-specific antigens for any fungus, including *H. capsulatum.*

Kits are provided which are suitable for use in performing the aforementioned assay methods to facilitate diagnosis of histoplasmosis in humans and other mammals. In one embodiment, an assay kit of the present invention can include labeled and/or unlabeled target fungus-specific antigen, as described above, in quantities sufficient to carry out the assays of the present invention. In another embodiment, an assay kit can include labeled and/or unlabeled antibodies to an target fungus-specific antigen, as described above, in quantities sufficient to carry out the assays of the present invention. In a further embodiment, an assay kit of the present invention can include both labeled and/or unlabeled target fungus-specific antigen and labeled and/or unlabeled antibody thereto, each as described above, in quantities sufficient to carry out the assays of the present invention. In any of the aforementioned embodiments, an assay kit can also further comprise known positive and/or negative control samples, other reagents useful in carrying out the assays of the present invention (e.g. radiolabeled secondary antibodies and/or enzyme-conjugated secondary antibodies along with the corresponding color-producing enzyme substrate therefore), and instructions for carrying out the assay methods. Kits as provided above may be utilized for any target fungus, including *H. capsulatum.*

The following example illustrates the invention, but is not to be taken as limiting the various aspects of the invention so illustrated.

EXAMPLE

MOLECULAR CLONING AND CHARACTERIZATION OF A RECOMBINANT HISTOPLASMA CAPSULATUM ANTIGEN FOR ANTIBODY DIAGNOSIS OF HUMAN HISTOPLASMOSIS

MATERIALS AND METHODS

Fungi and culture conditions. *H. capsulatum* G217B, a North American isolate, was obtained from the American Type Culture Collection (ATCC #26032, Rockville, Md.). Mycelial-phase organisms were cultured in a shaking water bath at 25° C. in broth containing 2% glucose and 1% yeast extract. Yeast-phase organisms were grown at 37° C. in HMM broth (Gibco-BRL, Gaithersburg, Md.) supplemented with 18.2 g of glucose, 1.0 g of glutamic acid (per liter), adjusted to pH 7.5 (17).

Human and animal sera. Human sera were obtained from patients with well-documented histoplasmosis (n=18), coccidioidomycosis (n=12), and candidiasis (n=5). Coccidioidomycosis sera were generously provided by Dr. Demothenes Pappagianis, University of California School of Medicine (Davis, Calif.). The histoplasmosis sera were obtained from patients with acute and chronic disease and from patients with disseminated infections (with positive bone marrow and/or blood cultures) associated with AIDS. The laboratory diagnosis of histoplasmosis infections was based on culture and biopsy results and/or serology tests (immunodiffusion and complement fixation with yeast and mycelial antigens). Blastomycosis sera from humans (n=5) and dogs (n=6) with documented clinical infections and sera from rabbits immunized with Blastomyces dermatitidis antigens or whole yeast cells (n=3) were a gift from Dr. Gene Scalerone (Idaho State College, Pocatello, Ind.).

Control human sera were obtained from healthy residents of St. Louis, Mo. A histoplasmosis serum pool was prepared with sera (n=12) from patients with proven histoplasmosis.

Isolation of *H. capsulatum* DNA. Genomic DNA from yeast cells was isolated essentially as previously described (17,34). Briefly, yeast cells were pelleted and resuspended in TE buffer (10 mM Tris, pH 8.0; 1 mM EDTA). SDS was added to 1% final concentration. DNA was extracted using phenol-chloroform, ethanol precipitated, and washed with 70% ethanol.

Mouse sera. Antibodies to yeast antigen or to a histidine fusion protein of the recombinant clone GH17 (GH17-his, see below) were produced in 6-week-old female BALB/c mice by foot-pad injection of 10 $\mu$g of yeast antigen or purified GH17-his in FCA followed by a second injection of antigen in IFA 4 weeks later. Sera were collected 1 week after the booster immunization.

Yeast antigen. Yeast cells were suspended in 0.01M Tris buffer (pH 8.3) containing protease inhibitors (1 mM phenyl methyl sulfonyl fluoride, 1 mM EDTA, 25 $\mu$g/ml N-tosyl-L-phenylalanine chloromethyl ketone, and 25 $\mu$g/ml N-a-p-tosyl-L-lysine chloromethyl ketone (all from Sigma Chemical Company, St. Louis, Mo.). The yeast homogenate was rocked at 4° C. overnight and centrifuged at 15,000×g for 10 min. The protein concentration in the supernatant was measured with a commercial kit (BCA; Pierce Chemical Co., Rockford, Ill.).

Screening of a gene expression library and selection of recombinant clones. A λgt11 cDNA library was custom-synthesized (Clontech Lab. Inc., Palo Alto, Calif.) using Poly(A)$^+$ mRNA derived from the mycelial stage of the G217B strain of *H. capsulatum.* This library has a recombinant frequency of over 90% after amplification. The DNA insert size range is 0.6–4.5 kb with an average size of 1.6 kb.

The library was immunoscreened to identify *H. capsulatum*-specific clones essentially as previously described (5,6). Clones that were reactive with antibodies in the histoplasmosis serum pool but not reactive with a normal human serum pool were selected and purified by repeated cycles of immunoselection. The reactivity of serum pools to fusion proteins expressed by purified recombinant phage was studied by plaque-dot immunoblot analysis as previously described (5). PCR was employed to amplify the cDNA inserts of selected recombinant λgt11 clones with the GenAmp DNA amplification kit (Perkin Elmer-Cetus, Norwalk, Conn.) as previously described (31). DNA dot hybridization was performed using peroxidase-labeled DNA fragments (14) to assess homology between the selected clones.

Southern blot analysis and DNA sequencing. *H. capsulatum* genomic DNA (5 μg) was cut with selected restriction endonuclease enzymes. Digestion products were electrophoresed in a 1% agarose gel and transferred to Hybond-N+ nylon transfer membrane (Amersham, Arlington Heights, Ill.) by standard techniques, and blots were probed with labeled cDNA insert of GH17 (26).

λgt11 DNA purified from GH17 was digested with EcoRI and ligated into pBluescript II SK-(Strategene Cloning Systems, La Jolla, Calif.) by standard methods (26), and plasmid DNA was prepared for DNA sequencing. The dideoxynucleotide chain termination method (32) was used for double stranded DNA sequencing using the TaqTrack Sequencing System (Promega Corporation, Madison, Wis.) with T3 and T7 pBluescript primers and with synthetic oligonucleotides.

The PC/GENE DNA Sequence Analysis Software (Intelligenetics, Mountain View, Calif.) and the BLAST Program (NCBI, NLM, NIH, Bethesda, Md.) were used to analyze nucleotide and deduced amino acid sequences and to determine sequence homologies with previously reported sequences in the GenBankm data base.

Expression and purification of GH17 in the pPROEX™-1 Protein Expression system. The cDNA insert of the recombinant clone GH17 was subcloned directionally into the plasmid expression vector pPROEX™-1 (Gibco-BRL) to produce a fusion protein containing 6 histidines. GH17 fusion protein (GH17-his) was purified from bacterial lysates by continuous-elution electrophoresis using a Bio-Rad Prep Cell (BioRad Laboratories, Hercules, Calif.). Briefly, a 10-ml overnight culture of *Escherichia coli* (BL21 strain) cells containing the recombinant plasmid GH17 was inoculated into 700 ml NZCYM medium (Gibco-BRL) containing 50 μg ampicillin per ml (Sigma). Cultures were grown at 37° C. with shaking to $OD_{600}$ of 1.0. IPTG (final concentration, 0.3 mM) was then added, and the culture was grown for an additional 5 h, after which the cells were pelleted and resuspended in 1:50 v/v of lysis buffer (10 mM $Na_2HPO_4$, 30 mM NaCl, 0.25% Tween 20, 10 mM EDTA, 10 mM EGTA, pH 7.0). The cells were frozen at −20° C. overnight. Cells were thawed in cold water and lysed by mild sonication. Cellular debris was removed by centrifugation at 10,000×g for 15 min. A 12% polyacrylamide gel was poured per the manufacturer's protocol for the BioRad Model 491 Prep Cell. Ten ml of sample in 1:1 loading buffer (0.0625M Tris-HCl, pH 6.8, 10% glycerol, 0.025% bromphenol blue) was loaded and the gel was run for 8 hrs at 12 W constant power. Three ml fractions were collected and run on 12% SDS-PAGE minigels (21). Western blots (35) were performed with the histoplasmosis human serum pool to identify fractions that contained the GH17 fusion protein. Three consecutive fractions containing the band of interest were selected, pooled, and dialyzed versus PBS, pH 7.2. The dialyzed protein was concentrated with a membrane concentrator (Centriplus,™ Amicon, Beverly, Mass.) and the protein concentration was measured with a commercial kit (BCA; Pierce Chemical Co.)

Immunoblot analysis of recombinant fusion proteins. *E. coli* Y1090 was infected at high density with recombinant phage on a thin layer of agarose over LB-agar to achieve confluent lysis, and synthesis of fusion proteins encoded by cDNA inserts was induced with IPTG-impregnated filters. The agarose layer containing bacterial lysate and fusion protein was then gently scrapped off and dissolved in SDS-PAGE sample buffer. SDS-PAGE was performed as described by Laemmli (21) at 135 V in 8% reducing gels. After SDS-PAGE, proteins were transferred electrophoretically (35) to nitrocellulose membranes. Membranes were then incubated in monoclonal antibody to β-galactosidase (Promega Biotech, Madison, Wis.) or in canine or human sera diluted 1:500 in PBS/T for 3 h at 37° C. Membranes were washed in PBS/T and incubated with alkaline phosphatase conjugated goat anti-mouse, anti-dog or anti-human IgG (Promega) for 1 h at 37° C. After washing, membranes were developed with NBT/BCIP.

Immunoblot analysis was carried out with *H. capsulatum* yeast extract to identify the native antigen(s) that correspond to the recombinant clone GH17. Yeast extract was separated by SDS-PAGE on 5–25% gradient slab gels and processed as described above with mouse antibody to GH17-his.

RESULTS

Selection of λgt11 clones that express *H. capsulatum*-specific antigens. Approximately, 500,000 phage plaques from an *H. capsulatum*-mycelia phase cDNA expression library were immunoscreened with a histoplasmosis serum pool and a normal control serum pool made from sera obtained from healthy residents of St. Louis who had no history of histoplasmosis. Twenty clones selected in the initial screen were rescreened with individual histoplasmosis sera. Eight highly immunoreactive clones were identified. These were again tested by plaque-dot immunoblots with sera from patients with other non-*H. capsulatum* fungal infections, including *C. immitis, B. derratitidis*, and Candida sp. Four clones that were reactive with antibodies in sera from histoplasmosis patients and not reactive with antibodies from patients with other fungal infections were selected for further study. DNA dot hybridization studies showed that all four clones hybridized to each other even under high stringency conditions (data not shown). The four clones designated as GH2, GH17, GH22 and GH23 produced a similar size β-galactosidase fusion protein with an apparent Mr of 140,000 vs. 116 kDa for unfused β-galactosidase (data not shown).

Molecular characterization of recombinant Histoplasma clones. The cDNA inserts of clones GH2, 17 and 22 were sequenced. All three clones contained identical 5' ends and an identical 633 bp open reading frame (ORF). That ORF is disclosed herein as SEQ ID NO:2. The three clones had variable amounts of untranslated DNA at the 3' ends (GH2-260 bp; GH17–142 bp; and GH22–166 bp). The complete nucleotide sequence of GH17 (GenBank™ Accession number U27588) is disclosed herein as SEQ ID NO:1. The deduced amino acid sequence of the translated protein is disclosed herein as SEQ ID NO:3. The presumed initiation codon 36 bp downstream from the 5' end is the first ATG in the ORF. The sequence also has a purine (adenine) in the −3 position (Kozak's rule), a prerequisite for an initiation codon (19). The initiation codon is followed by a hydrophobic sequence (predicted by hydropathy analysis, FIG. 2) which is consistent with a signal peptide sequence. Two potential signal peptidase cleavage sites were identified by the method of von Heijne (37) which predicts cleavage after residues 20 and 24. The sequence also contains a predicted transmembrane helix from amino acid 2 to 28 (28). The 3' non-coding region has a poly (A) tail of 14 bp. The ORF codes for a protein of 211 amino acids with a predicted size of 23.5 kDa and a calculated pI of 4.15. There are three potential N-glycosylation sites in the predicted amino acid sequence; these are located in the hydrophilic domains of the protein (boxed areas, FIG. 1). The GH17 sequence does not exhibit significant similarity to any proteins present in GenBank/EMBL sequence databases except for the similarity of the threonine-rich region to other threonine rich sequences such as cellulase of *Caldocellum saccharolyticum* (25), Xenopus laevis integumentary mucin (12), and a *Leishmania surface* antigen (27) (FIG. 1).

Figure 3:
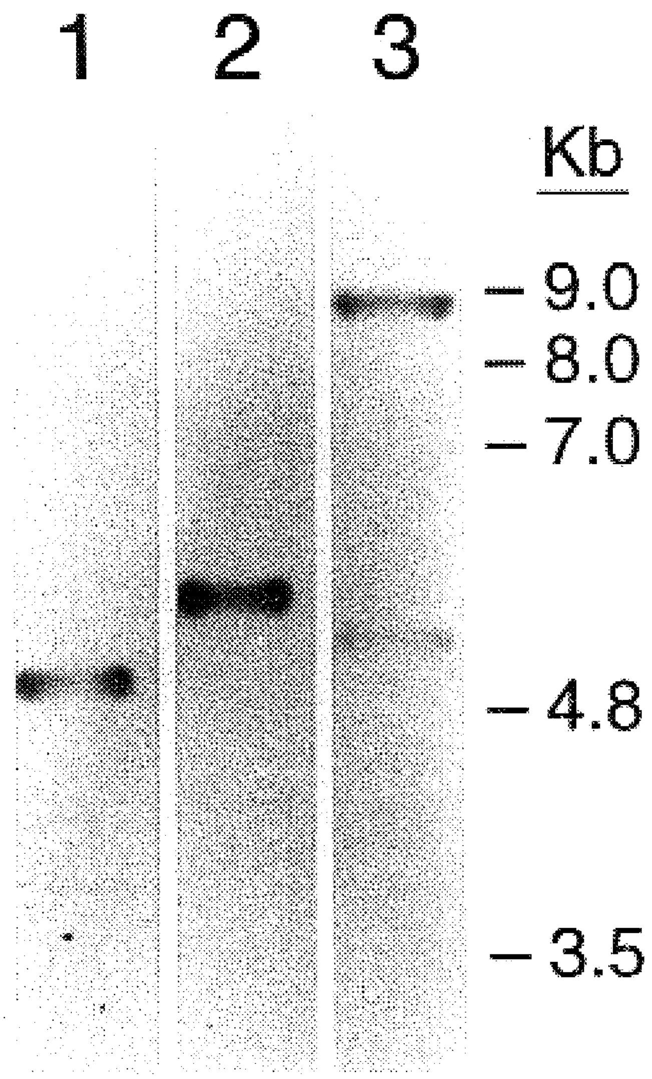
FIG. 3 shows a Southern blot of genomic DNA of *H. capsulatum* probed with labeled cDNA insert from clone GH17. Genomic DNA was digested with EcoRI (lane 1), PstI (lane 2), and SacI (lane 3), electrophoresed on a 1% agarose gel, and transferred to nylon membrane. The membrane was probed with peroxidase-labeled CDNA insert of GH17 and washed under high-stringency conditions.

Southern blot analysis was performed to identify genomic fragments carrying the gene(s) encoding the recombinant clone GH17. When DNA was cut with EcoRI and PstI and probed with labeled cDNA insert of GH17, bands were detected at 4.9 kb and 5.5 kb, respectively (FIG. 3). The probe hybridized to two bands (8.5 kb and 5.0 kb) in SacI digested DNA. However, recombinant clone GH17 has an internal SacI site. These results suggest a single location in the *H. capsulatum* genome for GH17.

Figure 4A:
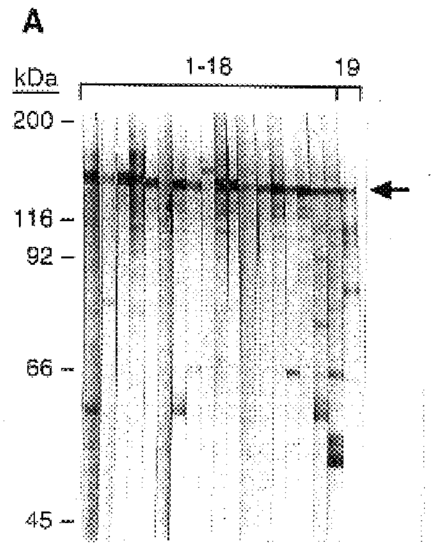
FIG. 4A shows a representative immunoblot demonstrating the immunoreactivity of the fusion protein. Bacterial cell-lysates from cells infected with GH17 were separated by SDS-PAGE and electrophoretically transferred to nitrocellulose paper. The blot was developed with individual sera from patients with histoplasmosis (Lanes 1–18). 16 of 18 sera had strong antibody reactivity with the fusion protein, and two sera were weakly reactive (Lanes 6 and 9). Lane 19 was developed with a murine monoclonal antibody to β-galactosidase.
Figure 4B:
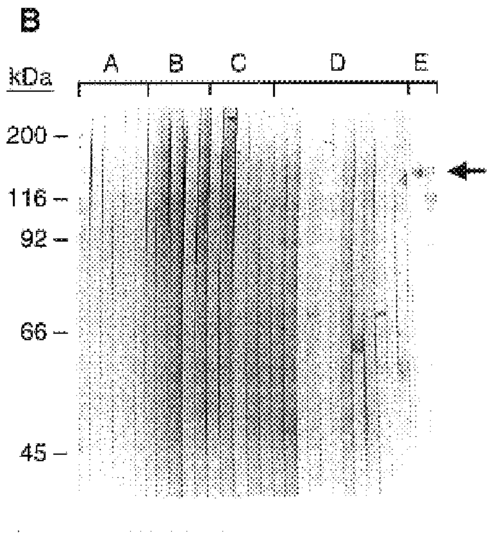
FIG. 4B demonstrates the antigenic specificity of recombinant *H. capsulatum* clone GH17β-galactosidase fusion protein by immunoblot analysis. Lanes in various panels were developed as follows: Panel A, with sera from dogs infected with *B. dermatitidis* (n=6); B, with human sera from patients infected with *B. dermatitidis* (n=5); C, with human sera from patients infected with Candida albicans (n=5); D, with human sera from patients infected with *Coccidioides immitis* (n=12); E, with human histoplasmosis serum pool and anti-β-galactosidase antibody, respectively.

Sensitivity and specificity of IgG antibodies to recombinant *H. capsulatum* proteins. Immunoreactivity of recombinant *H. capsulatum* proteins produced by clones GH2, 17, 22, 23 was assessed by Western blot with sera from patients with a variety of fungal infections. Most sera from histoplasmosis patients had easily visible antibody reactivity with all 4 recombinant proteins (Table 1, FIG. 4A). The sensitivity of Western blot with these clones for histoplasmosis sera ranged from 89–100% (Table 1, FIG. 4A). None of these clones was recognized by sera from humans and animals infected with other fungi (FIG. 4B).

TABLE 1

Sensitivity[a] and Specificity of Immunoblot with Recombinant *H. capsulatum* Clones

| | Clones | | | |
|---|---|---|---|---|
| Serum Source | GH2 | GH17 | GH22 | GH23 |
| Histoplasmosis | | | | |
| Human | 18/18[b] | 18/18 | 16/18 | 16/18 |
| Blstomycosis | | | | |
| Dog | 0/6 | 0/6 | 0/6 | 0/6 |
| Rabbit | 0/3 | 0/3 | 0/3 | 0/3 |
| Human | 0/5 | 0/5 | 0/5 | 0/5 |
| Coccidioidomycosis | | | | |
| Human | 0/12 | 0/12 | 0/12 | 0/12 |
| Candidiasis | | | | |
| Human | 0/5 | 0/5 | 0/5 | 0/5 |
| Uninfected Controls | | | | |
| Human | 0/12 | 0/12 | 0/12 | 0/12 |

[a]Immunoreactivity was assessed by immunoblot with β-galactosidase fusion proteins.
[b]No. of sera reactive/no. of sera tested.

Figure 5A:
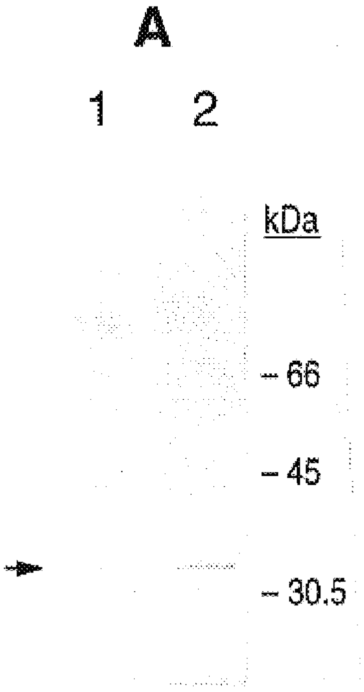
Figure 5B:
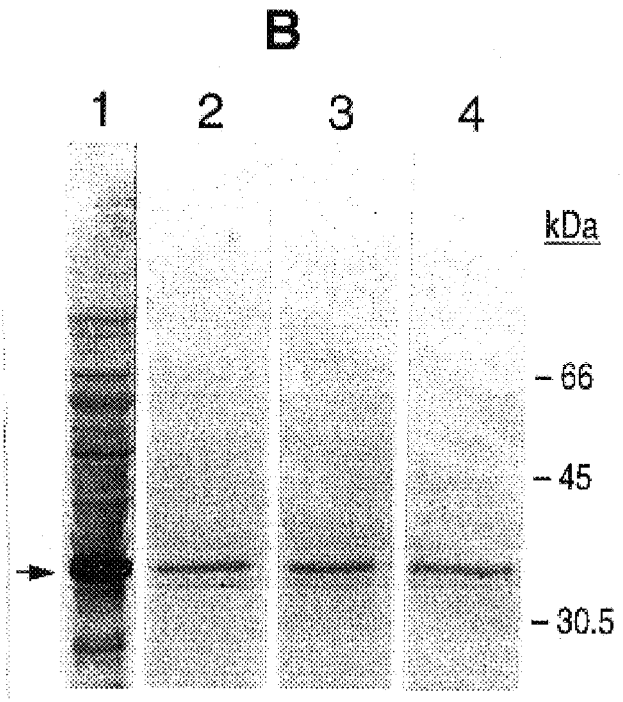
FIG. 5B shows immunoblot analysis of eluted fractions of GH17-his fusion protein separated by preparative SDS-PAGE in the model 491 BioRad Prep Cell. Aliquots (10 μl) from the Prep Cell fractions were separated by SDS-PAGE on 12% gels, immunoblotted, and developed as described for FIG. 5*a*. Lane 1, IPTG induced *E. coli* extract (2 μl); Lanes 2–4 contain positive fractions from the Prep Cell.

Expression of GH17 in pPROEX™-1 expression vector. The CDNA insert of GH17 was expressed as histidine fusion in the pPROEX™-1 protein expression system. Plasmid pPROEX-1 consists of a Trc promotor for high level expression in *E. coli*, a prokaryotic ribosome binding site, and a 6× His affinity tag for ease of purification. A fusion protein with an apparent size of 32 kDa was evident by SDS-PAGE and immunoblot (FIG. 5A). GH17-his failed to bind to a metal affinity column. Therefore, the fusion protein was purified from bacterial lysates by continuous-elution electrophoresis using a BioRad PrepCell. Western blots were performed to select fractions of interest by immunoblotting with a human histoplasmosis serum pool (FIG. 5B). Three consecutive fractions containing the band of interest were selected, pooled and dialyzed. This yielded a total of 500 μg of purified protein from approximately 700 ml of bacterial culture.

Pilot studies were carried out to test the purified GH17-his protein in an ELISA format (data not shown). Unfortunately, ELISA based on the GH17-his protein was less sensitive and specific than the recombinant immunoblot assay with the GH17-β-galactosidase fusion protein. This lowered specificity and sensitivity is believed to be due to cross-reactivity to the polyhistidine component of the GH17-his protein.

Figure 6:
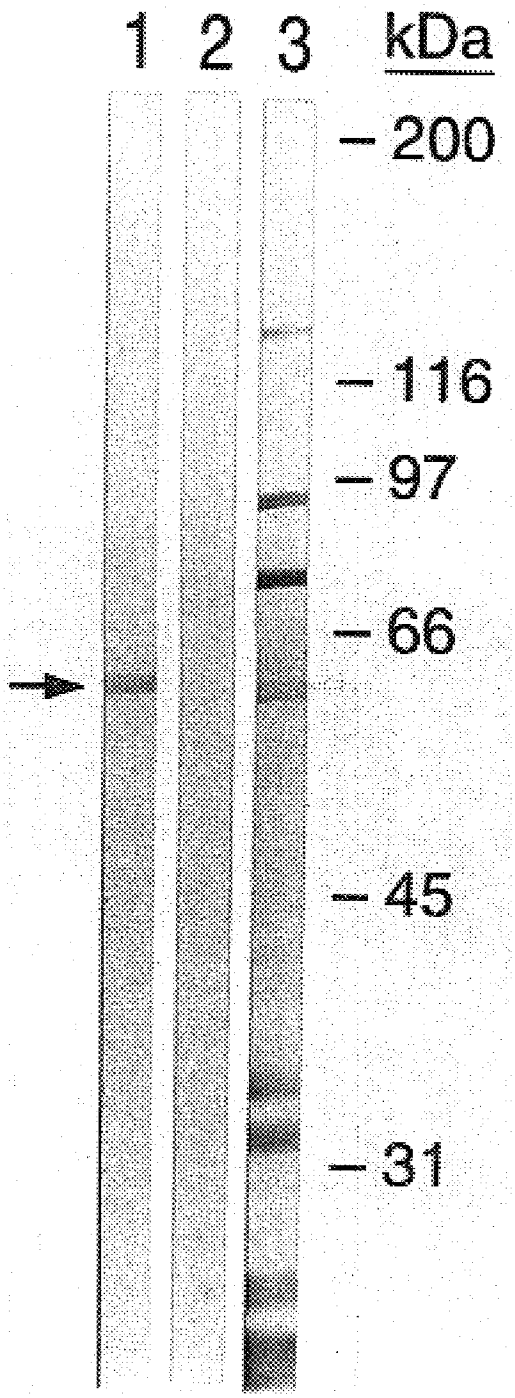
FIG. 6 shows an immunoblot analysis of *H. capsulatum* yeast antigen extract developed with: lane 1, mouse antibody to GH17-his fusion protein (1:500); lane 2, normal mouse serum (1:500); and lane 3, mouse antibodies to *H. capsulatum* yeast extract (1:500).

Inmunoblot analysis of mouse antibodies to recombinant antigen. Sera from mice immunized with GH17-his bound to a 60 kDa native *H. capsulatum* yeast antigen by Western blot (FIG. 6). This antigen was not recognized by pre-immune mouse sera.

DISCUSSION

The experiments of this Example demonstrate that *H. capsulatum*-specific antigens can be identified, cloned, characterized, and produced using recombinant DNA methodologies and other methods, as described. A recombinant *H. capsulatum* antigen was shown to have highly specific and sensitive immunodiagnostic potential.

Recombinant clones that expressed *H. capsulatum*-specific antigens were identified by several cycles of differential immunoscreening, and the most immunoreactive and specific clone (GH17) was selected for more detailed studies. GH17 codes for the most promising recombinant diagnostic antigen for histoplasmosis that has been identified to date. GH17 codes for a protein that corresponds to a 60 kDa native *H. capsulatum* antigen. There are three potential N-glycosylation sites [Asn-Asn/Lys-Thr] in the predicted amino acid sequence of GH17 (boxed areas, FIG. 1). Glycosylation at these sites could account for the difference between the predicted polypeptide mass of 23.5 kDa and the observed size of the native yeast protein recognized by the mouse antibodies to GH17 histidine fusion protein (60 kDa).

The protein encoded by GH17 is highly antigenic in humans with histoplasmosis. Chou-Fasman predictions based on the deduced amino acid sequence of GH17 (7) indicate that the protein is rich in potential B cell epitopes. These predictions are based principally on the hydrophilic character and accessibility of highly charged and exposed polar residues that comprise the turns and alpha helices within the predicted GH17 protein (13,20). Our results with human sera are consistent with these predictions. GH17 produced a 140 kDa fusion protein that was recognized in Western blots by 18 of 18 sera from patients with histoplasmosis.

In contrast to previous serological work with *H. capsulatum* (15, 16, 36, 40, 41) the GH17 recombinant immunoblot assay appears to have excellent specificity for histoplasmosis.

As shown in the Example, the present invention provides a method to isolate specific fungal antigens. In particular, the present invention offers significant advantages over prior art fungal antigens, antibodies and diagnostic methods employing the same. The specificity of the present target fungus antigens and antibodies make them particularly advantageous for reliable determination of the presence of the target fungus or antibodies which are specific to the target fungus. As applied to target fungi which are pathogens of vertebrates, such as *H. capsulatum*, use of antigens and antibodies of the present invention are useful for providing reliable evidence of present or past infection with *H. capsulatum*. Other features, objects and advantages of the present invention will be apparent to those skilled in the art. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

REFERENCES

1. Ajello, J. 1971. Coccidioidomycosis and histoplasmosis: a review of their epidemiology and geographical distribution. Mycopathol. Appl. 45:221–230.
2. Bauman, D. S., and C. D. Smith. 1975. Comparison of immunodiffusion and complement fixation tests in the diagnosis of histoplasmosis. J. Clin. Microbiol. 2:77–80.
3. Buechner, H. A., J. H. Seabury, and C. C. Campbe 11. 1973. The current status of serologic, immunologic, and skin tests in the diagnosis of pulmonary mycoses. Chest 63:259–270.
4. Chandler, J. W., T. K. Smith, and W. M. Newberry. 1969. Immunology of mycoses. II. Characterization of the immunoglobulin and antibody responses in histoplasmosis. J. Infect. Dis. 119:247–254.
5. Chandrashekar, R., K. Masood, R. M. Alvarez, A. F. Ogunrinade, R. Lujan, F. Richards, and G. J. Weil. 1991. Molecular cloning and characterization of recombinant parasite antigens for immunodiagnosis of onchocerciasis. J. Clin. Invest. 8:1460–1466.
6. Chandrashekar, R., K. C. Curtis, R. M. Ramzy, F. Liftis, B. W. Li, and G. J. Weil. 1994. Molecular cloning of Brugia malayi antigens for diagnosis of lymphatic filariasis. Mol. Biochem. Parasitol. 64:261–271.
7. Chou, P. Y., and G. Fasman. 1978. Prediction of the secondary structure of proteins from their amino acid sequence. Adv. Enzymol. Relat. Areas Mol. Biol. 47:145–147.
8. Edwards, P. Q., and E. L. Billings. 1971. World-wide pattern of skin sensitivity to histoplasmin. Am. J. Trop. Med. Hyg. 20:288–319.
9. George, R. B., R. S. Lambert, M. J. Bruce, T. W. Pickering, and R. M. Wolcott. 1981. Radioimmunoassay: a sensitive screening test for histoplasmosis and blastomycosis. Am. Rev. Resp. Dis. 124:407–410.
10. Goodwin, Jr., R., and R. M. Prez. 1978. Histoplasmosis. Am. Rev. Respir. Dis. 117:929–955.
11. Goodwin, R. A., Jr., and R. M. Des Perez. 1979. Histoplasmosis: State of the art. Am. Rev. Resp. Dis. 119:247–254.
12. Hauser, F. and W. Hoffman. 1992. P-domains as shuffled cysteine-rich modules in integumentary mucin C.1 (FIM-C.1) from Xenopus laevis. Polydispersity and genetic polymorphism. J. Biol. Chem. 267:24620–24624.
13. Hopp, T. P. 1986. Methods for identifying antigenic determinants and other interaction sites. J. Immunol. Methods. 88:1–18.
14. Kafatos, F. C., C. W. Jones, and A. Efstratiadis. 1979. Determination of nucleic acid sequence homologies by a dot hybridization procedure. Nucleic Acids Res. 7:1541–1552.
15. Kaufman L., and E. Reiss. 1986. Serodiagnosis of fungal diseases. p 446–466. In Rose, N. R., H. Friedman, and J. L. Fahey. Manual of Clinical Laboratory Immunology. 3rd edition. American Society for Microbiology, Washington, D.C.
16. Kaufman, L. 1992. Laboratory methods for the diagnosis and confirmation of systemic mycoses. Clin. Infect. Dis. 14:S23–S29.
17. Keath, E. J., A. A. Painter, G. S. Kobayashi, and G. Medoff. 1989. Variable expression of a yeast-phase-specific gene in Histoplasma capsulatum strains differing in thermotolerance and virulence. Infect. Immun. 57:1384–1390.
18. King, K. 1982. Histoplasmosis in Australia. Aust. Med. J. 2:550–551.
19. Kozak, M. 1986. Point mutations define a sequence flanking the AUG initiator codon that modulates translation by eukaryotic ribosomes. Cell 44:283–292.
20. Kyte, J., and R. F. Doolittle. 1982. A simple method for displaying the hydropathic character of a protein. J. Mol. Biol. 157:105–132.
21. Laemmli, U. K. 1970. Cleavage of structural proteins during the assembly of the head of bacteriophage T4. Nature 227:680–685.
22. Lambert, R. S., and R. B. George. 1987. Evaluation of enzyme immunoassay as a rapid screening test for histoplasmosis and blastomycosis. Am. Rev. Resp. Dis. 136:316–319.
23. Lobos, E., N. Weiss, M. Karam, H. R. Taylor, E. A. Ottesen, and T. B. Nutman. 1991. An immunogenic Onchocerca volvulus antigen: A specific and early marker of infection. Science 51:1603–1605.
24. Lustigman, S., B. Brotman, T. Huima, and A. M. Prince. 1991. Characterization of an Onchocerca volvulus cDNA clone encoding a genus-specific antigen present in infective larvae and adult worms. Mol. Biochem. Parasitol. 45:65–76.
25. Luthi, E., Jasmat, N. B., R. A. Grayling, D. R. Love, and P. L. Bergquist. 1991. Cloning, sequence analysis, and expression in Escherichia coli of a gene coding for a beta-mannose from the extremely thermophilic bacterium Caldocellum saccharolyticum. Appl. Environ. Microbiol. 57:694–700.
26. Maniatis, T. E., F. Fritsch, and J. Sambrook. 1982. Molecular cloning: A laboratory manual. Cold Spring Harbor Laboratory, Cold Spring Harbor, NY.
27. Murray, P. J. and T. W. Spithill. 1991. Variants of a Leishmania surface antigen derived from a multigenic family. J. Biol. Chem. 266:24477–24484.
28. Rao, M. J. K., and Argos, P. 1986. A conformational preference parameter to predict helices in integral membrane proteins. Biochem. Biophys. Acta. 869:197–214.
29. Rao, A., R. Forgan-Smith, G, Ritchie, H. Sakellaris, S. Miller, M. Arghyros. 1988. A serendipitous isolate of Histoplasma capsulatum. Pathology 20:191–193.
30. Reiss, E., H., H. Hutchinson, L. Pine, D. W. Zeigler, and L. Kaufman. 1977. Solid-phase competitive-binding radioimmunoassay for detecting antibody to the M antigen of histoplasmin. J. Clin. Microbiol. 6:598–604.
31. Saiki, R. K., D. H. Gelfand, S. Stoffel, S. Scharf, R. Higuchi, G. T. Horn, K. B. Mullis, and H. A. Erlich. 1988. Primer-directed enzymatic amplification of DNA with a thermostable DNA polymerase. Science 239:489–491.
32. Sanger, F., S. Nicklen, and A. R. Coulson. 1977. DNA sequencing with chain terminating inhibitors. Proc. Natl. Acad. Sci. USA. 74:5463–5467.
33. Schwarz, L. 1981. Histoplasmosis. Praeger Science Press, New York.

34. Spitzer, E. D., E. J. Keith, S. J. Travis, A. A. Painter, G. S. Kobayashi, and G. Medoff. 1990. Temperature-sensitive variants of *Histoplasma capsulatum* isolated from patients with acquired immunodeficiency syndrome. J. Infect. Dis. 162:258–261.
35. Towbin, H., T. Staehelin, and J. Gordon. 1979. Electrophoretic transfer of proteins from polyacrylamide gels to nitrocellulose sheets: procedure and some applications. Proc. Natl. Acad. Sci. USA. 76:4350–4354.
36. Vijayakumar, B., G. Medoff, G. S. Kobayashi, and W. L. Sieling. 1985. Cross-reacting human and rabbit antibodies to antigens of *Histoplasma capsulatum, Candida albicans*, and *Saccharomyces cerevisiae*. Infect. Immun. 48:806–812.
37. Von Heijne, G. 1986. A new method for predicting signal sequence cleavage sites. Nucleic Acids Res. 14:4683–4690.
38. Wheat, L. J., R. B. Kohler, M. L. V. French, J. Garten, A. White, and Z. Brahmi. 1983. IgM and IgG histoplasmal antibody response in histoplasmosis. Am. Rev. Resp. Dis. 128:65–70.
39. Wheat L. J., R. B. Kohler, and R. P. Tiwari. 1986. Diagnosis of disseminated histoplasmosis by detection of *Histoplasma capsulatum* antigen in serum and urine specimens. N. Eng. J. Med. 314:83–88.
40. Wheat L. J., P. Connolly-Stringfield, R. B. Kohler, P. T. Frame, and M. R. Gupta. 1989. *Histoplasma capsulatum polysaccharide antigen* detection in diagnosis and management of disseminated histoplasmosis in patients with AIDS. Am. J. Med. 87:396–400.
41. Wheat, L. J., R. B. Kohler, R. P. Tiwari, M. Garten, and M. L. V. French. 1989. Significance of Histoplasma antigen in the cerebrospinal fluid of patients with meningitis. Arch. Int. Med. 149:302–304.

We claim:

1. A method for determining the presence or absence of *H. capsulatum* antibodies in a mammal, the method comprising:

obtaining an antibody-containing sample from the mammal, contacting the sample with a protein antigen of *H. capsulatum* which has an amino acid sequence that includes a portion at least five amino acids in length of the amino acid sequence set forth in SEQ ID NO: 3, and which portion is bound by antibodies to *H. capsulatum* but which is not substantially bound by antibodies to *Coccidioides immitis, Blastomyces* dermatitidis and Candida sp., and determining whether an antibody in the sample immunoreacts with the protein antigen of *H. capsulatum.*

2. The method of claim 1 wherein the mammal is a human.

3. The method of claim 1 wherein the immunoreactivity of the antibodies to *Coccidioides immitis, Blastomyces dermatitidis* and Candida sp. is less than about 10% of the immunreactivity of the antibodies to *H. capsulatum* with the protein antigen of *H. capsulatum.*

4. The method of claim 1 wherein the immunoreactivity of the antibodies to *Coccidioides immitis, Blastomyces dermatitidis* and Candida sp. with the protein antigen of *H. capsulatum* is less than about 1% of the immunoreactivity of the antibodies to *H. capsulatum* with the protein antigen of *H. capsulatum.*

5. The method of claim 1 wherein the immunoreactivity of the antibodies to *Coccidioides immitis, Blastomyces dermatitidis* and Candida sp. with the protein antigen of *H. capsulatum* is less than about 5% of the immunoreactivity of the antibodies to *H. capsulatum* with the protein antigen of *H. capsulatum.*

6. The method of claim 1 wherein immunoreactivity of the antibodies to *Coccidioides immitis, Blastomyces dermatitidis* and Candida sp. with the protein antigen of *H. capsulatum* is less than about 2% of the immunoreactivity of the antibodies to *H. capsulatum* with the protein antigen of *H. capsulatum.*

7. The method of claim 1 wherein the protein antigen of *H. capsulatum* is substantially free of non-protein determinants.

8. The method of claim 1 wherein the protein antigen of *H. capsulatum* is substantially free of carbohydrate determinants and phosphorylcholine.

9. The method of claim 1 wherein the method comprises an assay selected from the group consisting of a precipitin-based immunoassay, an indirect label-based immunoassay, a direct label-based immunoassay and an inhibition/competitive-type label-based immunoassay.

* * * * *

SEQUENCE LISTING

```
<160> NUMBER OF SEQ ID NOS: 9

<210> SEQ ID NO 1
<211> LENGTH: 810
<212> TYPE: DNA
<213> ORGANISM: Histoplasma capsulatum

<400> SEQUENCE: 1

acacagcata acagaagatc tctgaaattg acaaaaatga aaaccatttg cttgcctgct      60

tacttcaagc ttctctcttt tctgtctgct atagctgtga catctggagc agctgttgac     120

tcctgtctct tagaatcaaa ctgcccaccg ccaacaacaa caacgacaac aacgacaaca     180

acaccaacac caacaccaac atcaataata ccaataacac caatagtacc agcaaataag     240

acaattgtgc ttacaaccac tattgagcct gggccaggcc aggtttgggc gcaaatagag     300

gagattgatc ctgaaccata ttatgttaga tgggtccctg atccaacgtt tgccacgcct     360

gttgtactgc acaataacac agatcttgtc ttcatggatg gaagcaaatc tttttatctc     420

aacttcgata acagcacctc tgacacgggt atttattttg tgaaccttaa ctccaacgct     480

ggtattagtc aactctataa ggatagtgac aacaagttgc tctggggtgg agctcaacaa     540

gagcgggatg gctggatgtg gtgcttcatg gtcgatctac aataccgcat gttctattct     600

gacagtaaat tcgttggttc tccaagggat tgtggcctct cctctgtctt tttgacagag     660

cgcccgagtt gaaacagcta ttgtgaggag gggagcagtt ctggaccggc cgtgcgaaat     720

aagtaatgag tatcaaagtg tttctgtgat ctatgaaatt tagagggcca ggatacaatt     780

attgatcaac tcccacaaaa aaaaaaaaaa                                       810

<210> SEQ ID NO 2
<211> LENGTH: 631
<212> TYPE: DNA
<213> ORGANISM: Histoplasma capsulatum

<400> SEQUENCE: 2

atgaaaacca tttgcttgcc tgcttacttc aagcttctct cttttctgtc tgctatagct      60

gtgacatctg gagcagctgt tgactcctgt ctcttagaat caaactgccc accgccaaca     120

acaacaacga caacaacgaa caccaacacc aacaccaaca tcaataatac caataacacc     180

aatagtacca gcaaataaga caattgtgct tacaaccact attgagcctg ggccaggcca     240

ggtttgggcg caaatagagg agattgatcc tgaaccatat tatgttagat gggtccctga     300
```

-continued

```
tccaacgttt gccacgcctg ttgtactgca caataacaca gatcttgtct tcatggatgg    360

aagcaaatct ttttatctca acttcgataa cagcacctct gacacgggta tttattttgt    420

gaaccttaac tccaacgctg gtattagtca actctataag gatagtgaca acaagttgct    480

ctggggtgga gctcaacaag agcgggatgg ctggatgtgg tgcttcatgg tcgatctaca    540

ataccgcatg ttctattctg acagtaaatt cgttggttct ccaagggatt gtggcctctc    600

ctctgtcttt ttgacagagc gcccgagttg a                                   631


<210> SEQ ID NO 3
<211> LENGTH: 211
<212> TYPE: PRT
<213> ORGANISM: Histoplasma capsulatum

<400> SEQUENCE: 3

Met Lys Thr Ile Cys Leu Pro Ala Tyr Phe Lys Leu Leu Ser Phe Leu
1               5                   10                  15

Ser Ala Ile Ala Val Thr Ser Gly Ala Ala Val Asp Ser Cys Leu Leu
            20                  25                  30

Glu Ser Asn Cys Pro Pro Pro Thr Thr Thr Thr Thr Thr Thr Thr Thr
        35                  40                  45

Thr Pro Thr Pro Thr Pro Thr Ser Ile Ile Pro Ile Thr Pro Ile Val
    50                  55                  60

Pro Ala Asn Lys Thr Ile Val Leu Thr Thr Thr Ile Glu Pro Gly Pro
65                  70                  75                  80

Gly Gln Val Trp Ala Gln Ile Glu Glu Ile Asp Pro Glu Pro Tyr Tyr
                85                  90                  95

Val Arg Trp Val Pro Asp Pro Thr Phe Ala Thr Pro Val Val Leu His
            100                 105                 110

Asn Asn Thr Asp Leu Val Phe Met Asp Gly Ser Lys Ser Phe Tyr Leu
        115                 120                 125

Asn Phe Asp Asn Ser Thr Ser Asp Thr Gly Ile Tyr Phe Val Asn Leu
    130                 135                 140

Asn Ser Asn Ala Gly Ile Ser Gln Leu Tyr Lys Asp Ser Asp Asn Lys
145                 150                 155                 160

Leu Leu Trp Gly Gly Ala Gln Gln Glu Arg Asp Gly Trp Met Trp Cys
                165                 170                 175

Phe Met Val Asp Leu Gln Tyr Arg Met Phe Tyr Ser Asp Ser Lys Phe
            180                 185                 190

Val Gly Ser Pro Arg Asp Cys Gly Leu Ser Ser Val Phe Leu Thr Glu
        195                 200                 205

Arg Pro Ser
    210


<210> SEQ ID NO 4
<211> LENGTH: 25
<212> TYPE: PRT
<213> ORGANISM: Caldocellum saccharolyticum

<400> SEQUENCE: 4

Pro Thr Ser Thr Val Thr Pro Thr Pro Thr Pro Thr Pro Thr Pro Thr
1               5                   10                  15

Pro Thr Val Thr Ala Thr Pro Thr Pro
            20                  25
```

-continued

```
<210> SEQ ID NO 5
<211> LENGTH: 41
<212> TYPE: PRT
<213> ORGANISM: Leishmania

<400> SEQUENCE: 5

Pro Pro Thr Thr Thr Thr Thr Thr Thr Thr Thr Thr Thr Thr Thr Thr
1               5                   10                  15

Thr Thr Thr Lys Pro Pro Ile Thr Thr Ala Thr Thr Thr Lys Pro Pro
            20                  25                  30

Thr Thr Thr Thr Thr Thr Thr Lys Pro
        35                  40


<210> SEQ ID NO 6
<211> LENGTH: 57
<212> TYPE: PRT
<213> ORGANISM: Xenopus laevis

<400> SEQUENCE: 6

Thr Thr Lys Ala Thr Thr Thr Thr Pro Thr Thr Thr Thr Thr Thr Pro
1               5                   10                  15

Thr Thr Thr Thr Thr Thr Thr Thr Thr Thr Lys Ala Thr Thr Thr Thr
            20                  25                  30

Pro Thr Thr Thr Thr Pro Thr Thr Thr Thr Thr Lys Ala Thr Thr Thr
        35                  40                  45

Thr Pro Thr Thr Thr Thr Thr Thr Pro
    50                  55


<210> SEQ ID NO 7
<211> LENGTH: 25
<212> TYPE: PRT
<213> ORGANISM: Histoplasma Capsulatum

<400> SEQUENCE: 7

Pro Pro Thr Thr Thr Thr Thr Thr Thr Thr Thr Thr Pro Thr Pro Thr
1               5                   10                  15

Pro Thr Ser Ile Ile Pro Ile Thr Pro
            20                  25


<210> SEQ ID NO 8
<211> LENGTH: 41
<212> TYPE: PRT
<213> ORGANISM: Histoplasma Capsulatum

<400> SEQUENCE: 8

Pro Pro Thr Thr Thr Thr Thr Thr Thr Thr Thr Thr Pro Thr Pro Thr
1               5                   10                  15

Pro Thr Ser Ile Ile Pro Ile Thr Pro Ile Val Pro Ala Asn Lys Thr
            20                  25                  30

Ile Val Leu Thr Thr Thr Ile Glu Pro
        35                  40


<210> SEQ ID NO 9
<211> LENGTH: 57
<212> TYPE: PRT
<213> ORGANISM: Histoplasma Capsulatum

<400> SEQUENCE: 9

Thr Ser Gly Ala Ala Val Asp Ser Cys Leu Leu Glu Ser Asn Cys Pro
1               5                   10                  15
```

-continued

```
Pro Pro Thr Thr Thr Thr Thr Thr Thr Thr Thr Thr Pro Thr Pro Thr
            20                  25                  30

Pro Thr Ser Ile Ile Pro Ile Thr Pro Ile Val Pro Ala Asn Lys Thr
        35                  40                  45

Ile Val Leu Thr Thr Thr Ile Glu Pro
    50                  55
```